(12) United States Patent
Chen et al.

(10) Patent No.: US 10,675,250 B1
(45) Date of Patent: Jun. 9, 2020

(54) NANOPARTICLE, PREPARATION PROCESS AND USES THEREOF

(71) Applicant: National Tsing Hua University, Hsinchu (TW)

(72) Inventors: Yun-Ching Chen, Hsinchu (TW); Chih-Chun Chang, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 16/366,630

(22) Filed: Mar. 27, 2019

(30) Foreign Application Priority Data

Dec. 22, 2018 (TW) .............................. 107146673 A

(51) Int. Cl.
| A61K 9/00 | (2006.01) |
| A61K 9/51 | (2006.01) |
| A61K 33/32 | (2006.01) |
| A61P 35/00 | (2006.01) |
| A61K 31/44 | (2006.01) |

(52) U.S. Cl.
CPC .......... *A61K 9/5115* (2013.01); *A61K 9/5192* (2013.01); *A61K 31/44* (2013.01); *A61K 33/32* (2013.01); *A61P 35/00* (2018.01)

(58) Field of Classification Search
CPC .................................................... A61K 9/5115
See application file for complete search history.

(56) References Cited

PUBLICATIONS

Gong, Core-Shell TaOx@MnO2 nanoparticles as a nanoradiosensitizer for effective cancer radiotherapy, Journal of Materials Chemistry B, 2018, 6, 2250-2257.*

* cited by examiner

*Primary Examiner* — Paul W Dickinson
(74) *Attorney, Agent, or Firm* — WPAT, PC

(57) ABSTRACT

The present disclosure provides a nanoparticle, a preparation process thereof, a method for enhancing effect of a liver cancer drug, and a method for ameliorating tumor hypoxia by using the nanoparticle.

12 Claims, 36 Drawing Sheets

Specification includes a Sequence Listing.

SEQUENCE LISTING

<160> NUMBER OF SEQ ID NOS: 21

<210> SEQ ID NO 1
<211> LENGTH: 12
<212> TYPE: PRT
<213> ORGANISM: Artificial Sequence
<220> FEATURE:
<223> OTHER INFORMATION: synthetic peptide

<400> SEQUENCE: 1

Ser Phe Ser Ile Ile His Thr Pro Ile Leu Pro Leu
1               5                   10

<210> SEQ ID NO 2
<211> LENGTH: 19
<212> TYPE: DNA
<213> ORGANISM: Artificial Sequence
<220> FEATURE:
<223> OTHER INFORMATION: synthetic primer

<400> SEQUENCE: 2
agcgcagtct taccgaagg                                                  19

<210> SEQ ID NO 3
<211> LENGTH: 23
<212> TYPE: DNA
<213> ORGANISM: Artificial Sequence
<220> FEATURE:
<223> OTHER INFORMATION: synthetic primer

<400> SEQUENCE: 3
tcgctgcttt catactgaac ttt                                            23

<210> SEQ ID NO 4
<211> LENGTH: 19
<212> TYPE: DNA
<213> ORGANISM: Artificial Sequence
<220> FEATURE:
<223> OTHER INFORMATION: synthetic primer

<400> SEQUENCE: 4
tgtgaccagc aacacggtg                                                 19

<210> SEQ ID NO 5
<211> LENGTH: 20
<212> TYPE: DNA
<213> ORGANISM: Artificial Sequence
<220> FEATURE:
<223> OTHER INFORMATION: synthetic primer

<400> SEQUENCE: 5
acaacaggag agtagggcgc                                                20

<210> SEQ ID NO 6
<211> LENGTH: 22
<212> TYPE: DNA
<213> ORGANISM: Artificial Sequence
<220> FEATURE:
<223> OTHER INFORMATION: synthetic primer

<400> SEQUENCE: 6
cttgaacgga aagtggaatc ct                                             22

<210> SEQ ID NO 7
<211> LENGTH: 19
<212> TYPE: DNA
<213> ORGANISM: Artificial Sequence
<220> FEATURE:
<223> OTHER INFORMATION: synthetic primer

<400> SEQUENCE: 7
gtcaggcttg gaaacgtcc                                                 19

<210> SEQ ID NO 8
<211> LENGTH: 25
<212> TYPE: DNA
<213> ORGANISM: Artificial Sequence
<220> FEATURE:
<223> OTHER INFORMATION: synthetic primer

<400> SEQUENCE: 8
cagtcatagg gagctgtcta ccaaa                                          25

<210> SEQ ID NO 9
<211> LENGTH: 20
<212> TYPE: DNA
<213> ORGANISM: Artificial Sequence
<220> FEATURE:
<223> OTHER INFORMATION: synthetic primer

<400> SEQUENCE: 9
gggtacacgc tgggaaacat                                               20

<210> SEQ ID NO 10
<211> LENGTH: 20
<212> TYPE: DNA
<213> ORGANISM: Artificial Sequence
<220> FEATURE:
<223> OTHER INFORMATION: synthetic primer

<400> SEQUENCE: 10
aaaagcagaa gcaccaggaa                                               20

<210> SEQ ID NO 11
<211> LENGTH: 20
<212> TYPE: DNA
<213> ORGANISM: Artificial Sequence
<220> FEATURE:
<223> OTHER INFORMATION: synthetic primer

<400> SEQUENCE: 11
ggcccatcta gaccattgtg                                               20

<210> SEQ ID NO 12
<211> LENGTH: 19
<212> TYPE: DNA
<213> ORGANISM: Artificial Sequence
<220> FEATURE:
<223> OTHER INFORMATION: synthetic primer

<400> SEQUENCE: 12
cacacgctgc cttgtgtct                                                19

<210> SEQ ID NO 13
<211> LENGTH: 19
<212> TYPE: DNA
<213> ORGANISM: Artificial Sequence
<220> FEATURE:
<223> OTHER INFORMATION: synthetic primer

<400> SEQUENCE: 13
ggtcagcaaa agcacggtt                                                19

<210> SEQ ID NO 14
<211> LENGTH: 23
<212> TYPE: DNA
<213> ORGANISM: Artificial Sequence
<220> FEATURE:
<223> OTHER INFORMATION: synthetic primer

<400> SEQUENCE: 14
tggtcaagaa acatttcaac gcc                                           23

<210> SEQ ID NO 15
<211> LENGTH: 23
<212> TYPE: DNA
<213> ORGANISM: Artificial Sequence
<220> FEATURE:
<223> OTHER INFORMATION: synthetic primer

<400> SEQUENCE: 15
ggtgaggatc tctggttttg gta                                           23

<210> SEQ ID NO 16
<211> LENGTH: 23

```
<212> TYPE: DNA
<213> ORGANISM: Artificial Sequence
<220> FEATURE:
<223> OTHER INFORMATION: synthetic primer

<400> SEQUENCE: 16
attgcacatc agactttgag gaa                                              23

<210> SEQ ID NO 17
<211> LENGTH: 20
<212> TYPE: DNA
<213> ORGANISM: Artificial Sequence
<220> FEATURE:
<223> OTHER INFORMATION: synthetic primer

<400> SEQUENCE: 17
ataatggccg tgtcgcttcg                                                  20

<210> SEQ ID NO 18
<211> LENGTH: 20
<212> TYPE: DNA
<213> ORGANISM: Artificial Sequence
<220> FEATURE:
<223> OTHER INFORMATION: synthetic primer

<400> SEQUENCE: 18
ctgccctcgg acaagctgag                                                  20

<210> SEQ ID NO 19
<211> LENGTH: 20
<212> TYPE: DNA
<213> ORGANISM: Artificial Sequence
<220> FEATURE:
<223> OTHER INFORMATION: synthetic primer

<400> SEQUENCE: 19
ctagtgggac gcggacatgg                                                  20

<210> SEQ ID NO 20
<211> LENGTH: 24
<212> TYPE: DNA
<213> ORGANISM: Artificial Sequence
<220> FEATURE:
<223> OTHER INFORMATION: synthetic primer

<400> SEQUENCE: 20
actcgctagc atggcccacg agag                                             24

<210> SEQ ID NO 21
<211> LENGTH: 24
<212> TYPE: DNA
<213> ORGANISM: Artificial Sequence
<220> FEATURE:
<223> OTHER INFORMATION: synthetic primer

<400> SEQUENCE: 21
cgtgaattct cacttctgca cggg                                             24
```

NANOPARTICLE, PREPARATION PROCESS AND USES THEREOF

CROSS-REFERENCE TO RELATED APPLICATION

This application claims priority of Taiwan patent application No. 107146673, filed on Dec. 22, 2018, the content of which is incorporated herein in its entirety by reference.

BACKGROUND OF THE INVENTION

1. Field of the Invention

The present invention relates to a nanoparticle, a preparation process thereof, a method for enhancing effect of a liver cancer drug, and a method for ameliorating tumor hypoxia by using the nanoparticle.

2. The Prior Art

According to the American Cancer Society, liver cancer is the second leading cause of death in men. According to the National Cancer Institute, the 5-year survival rate of liver cancer from 2007 to 2013 was only 17.6% in the United States. In Taiwan, there were 11,358 new cases of liver cancer in 2014 and 8,179 deaths from liver cancer. Due to the high incidence and low survival rate of liver cancer, it is necessary to develop a strategy for the effective treatment of liver cancer.

The tyrosine kinase inhibitor, such as Sorafenib, is currently clinically used to block vascular endothelial growth factor receptor (VEGFR)/platelet-derived growth factor receptor (PDGFR) in the tumor microvasculature and the RAF/MEK/ERK pathway of liver cancer cells to inhibit angiogenesis and tumor development. In addition, Sorafenib is an approved drug for the treatment of advanced liver cancer, which can effectively improve the overall survival of patients with advanced liver cancer.

However, after treatment with Sorafenib, other acquired drug resistances, including autophagy, tumor hypoxia, crosstalk between signaling pathways, and epithelial-mesenchymal transition (EMT) are produced, in which tumor hypoxia not only causes cancer cells to change, but also causes drug resistance to chemotherapy or disables radiation therapy, and promotes the growth and metastasis of cancer cells, driving cancer cells toward a more malignant development. In order to alleviate the above-mentioned complications of drug resistance, researchers in the field are working to develop a combination drug of Sorafenib.

In addition, a gadolinium (Gd)-based contrast agent (CA) is often used clinically as a contrast agent for cancer magnetic resonance imaging (MRI). However, Gd-based contrast agents have been found to cause renal systemic fibrosis and accumulate in the patient's central nervous system and skin. Therefore, researchers in the field have actively developed a contrast agent for cancer magnetic resonance imaging that does not cause the above problems.

Nanoparticles (NPs) can be used clinically to deliver drugs (such as anticancer drugs) to target sites, and thus are considered to have high potential in the field of nanotechnology and medicine. In addition, the application of nanoparticles includes drug/gene delivery, photodynamic therapy, and MRI. The benefits of nanoparticles include tumor targeting ligands modifiability, low toxicity, and better pharmacokinetics compared to general drugs. However, conventional nanoparticles often suffer from poor biocompatibility, poor stability, and damage to normal tissues, and degradation before reaching the target site.

In order to solve the above problems, it is necessary to develop a novel nanoparticle which is excellent in biocompatibility and stability, does not cause damage to normal tissues, can alleviate tumor hypoxia, and a contrast agent for cancer magnetic resonance imaging, so that it will bring about considerable breakthroughs in the technology of the field for the benefit of a large group of people in need thereof.

SUMMARY OF THE INVENTION

A primary objective of the present invention is to provide a nanoparticle, comprising: a core comprising manganese dioxide and at least one negatively charged lipid carrier, wherein the negatively charged lipid carrier encapsulates the manganese dioxide, and the core is encapsulated in a polymer and a lipid by a multiple phase emulsion reaction to form the nanoparticle.

According to an embodiment of the present invention, the nanoparticle has a particle diameter ranging from 20 nm to 500 nm.

According to an embodiment of the present invention, the at least one negatively charged lipid carrier is 1,2-dioleoyl-sn-glycero-3-phosphate (DOPA).

According to an embodiment of the present invention, the nanoparticle further comprises an anti-angiogenesis drug, and the anti-angiogenesis drug is hydrophobic.

According to an embodiment of the present invention, the anti-angiogenesis drug is Sorafenib.

According to an embodiment of the present invention, the polymer is poly D,L-lactide-co-glycolic acid (PLGA).

According to an embodiment of the present invention, the lipid is an emulsifier or a stabilizer.

According to an embodiment of the present invention, the emulsifier is selected from the group consisting of D-α-Tocopherol polyethylene glycol 1000 succinate (TPGS), polyvinyl alcohol (PVA), and any combination thereof; and the stabilizer is selected from the group consisting of 1,2-distearoyl-sn-glycero-3-phosphoethanolamine-N-[methoxy(polyethylene glycol)-2000] (DSPE-PEG2000), 1,2-distearoyl-sn-glycero-3-phosphoethanolamine-N-[maleimide(polyethylene glycol)-2000] (DSPE-PEG Mal), cholesterol, 1,2-Dioleoyl-sn-glycero-3-phosphocholine (DOPC), and any combination thereof.

According to an embodiment of the present invention, the nanoparticle further comprises a target peptide, and the target peptide is a SP94 peptide.

According to an embodiment of the present invention, the core is a solid core.

According to an embodiment of the present invention, the nanoparticle is applied in a contrast agent for magnetic resonance imaging.

Another objective of the present invention is to provide a process to prepare a nanoparticle, comprising the steps of: (a) mixing a first microemulsion with a second microemulsion, and performing a reduction reaction to form a mixture, wherein the first microemulsion comprises ascorbic acid and sodium hydroxide, and the second microemulsion comprises at least one negatively charged lipid carrier and potassium permanganate; (b) subjecting the mixture to a first centrifugation to remove a supernatant and obtaining a core; and (c) encapsulating the core in a polymer and a lipid by a multiple phase emulsion reaction to form the nanoparticle; wherein the core comprises manganese dioxide and the negatively charged lipid carrier, and the negatively charged lipid carrier encapsulates the manganese dioxide.

According to an embodiment of the present invention, the process further comprises the step of mixing the nanoparticle with an anti-angiogenesis drug, so that the nanoparticle comprises the anti-angiogenesis drug, wherein the anti-angiogenesis drug is hydrophobic.

According to an embodiment of the present invention, the polymer is poly D,L-lactide-co-glycolic acid (PLGA).

According to an embodiment of the present invention, the lipid is an emulsifier or a stabilizer, and the nanoparticle is further subjected to a second centrifugation after the multiple phase emulsion reaction.

According to an embodiment of the present invention, the process further comprises the step of conjugating the nanoparticle with a target peptide, wherein the target peptide is a SP94 peptide.

Another objective of the present invention is to provide a method using the aforementioned nanoparticle for preparing a contrast agent for magnetic resonance imaging.

Another objective of the present invention is to provide a method for enhancing effect of a liver cancer drug, comprising administering to a subject in need thereof an agonist comprising an effective amount of the aforementioned nanoparticle.

Another objective of the present invention is to provide a method for ameliorating tumor hypoxia, comprising administering to a subject in need thereof a pharmaceutical composition comprising an effective amount of the aforementioned nanoparticle.

According to an embodiment of the present invention, the tumor hypoxia is liver tumor hypoxia.

According to an embodiment of the present invention, the nanoparticle reverses epithelial-mesenchymal transition (EMT) induced by the liver tumor hypoxia.

In summary, the nanoparticles of the present invention have the effect on good biocompatibility and stability, no damage to normal tissues, alleviation of tumor hypoxia, being used as an agonist for enhancing effect of a liver cancer drug, and as a contrast agent for cancer magnetic resonance imaging.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1A:
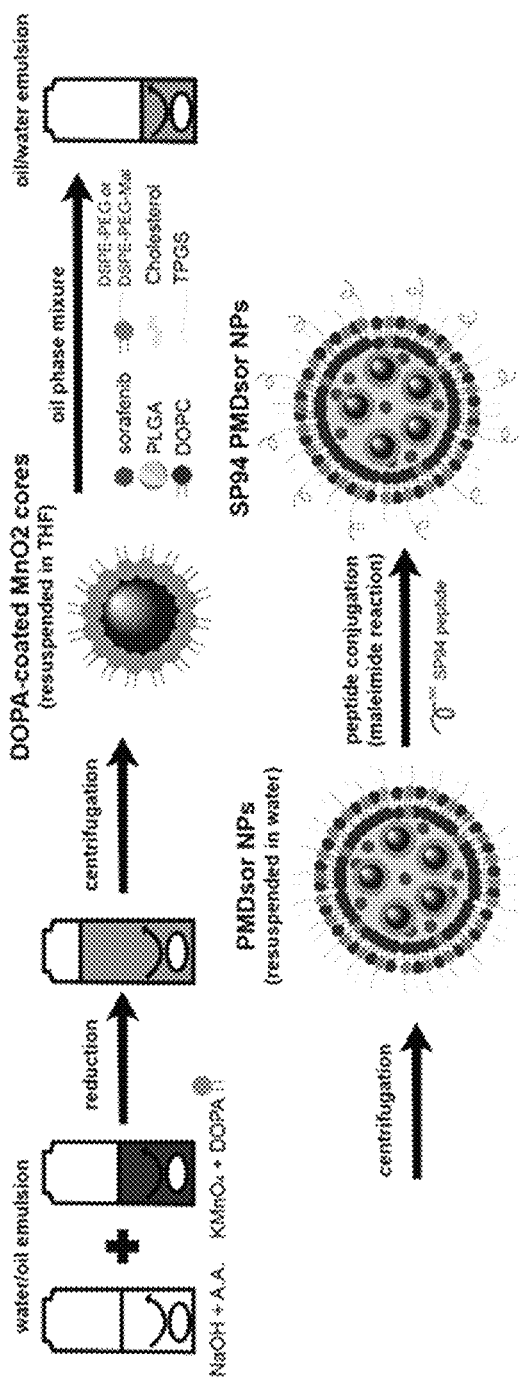
FIG. 1A is a process flow diagram showing the preparation of the nanoparticles of the present invention.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

As used herein, the term "nanoparticle" refers to a particle having a particle diameter less than 1 μm. Preferably, the nanoparticle of the present invention has a particle diameter between 20 nm and 500 nm.

As used herein, the term "agonist" refers to a molecule that directly, indirectly or substantially induces, promotes or enhances the biological activity or receptor activation of another molecule.

As used herein, the term "tumor hypoxia" refers to a physiological difference between the normal and the tumor tissue at the oxygen level, wherein the partial pressure of oxygen in the tumor tissue is reduced compared with that of the normal tissue.

As used herein, the term "SP94 peptide" refers to a hepatocellular carcinoma (HCC)-specific peptide ligand for the delivery of targeted drugs.

According to the present invention, the pharmaceutical composition can be made into a dosage form suitable for parenteral or oral administration using techniques well known to those skilled in the art, including, but not limited to, injection (e.g., sterile aqueous solution or dispersion), sterile powder, tablet, troche, pill, capsule, and the like.

According to the present invention, the pharmaceutical composition can be administered by a parenteral route selected from the group consisting of: intraperitoneal injection, subcutaneous injection, intramuscular injection, intravenous injection, sublingual administration, and transdermal administration.

According to the present invention, the pharmaceutical composition may further comprise a pharmaceutically acceptable carrier widely used in pharmaceutically manufacturing techniques. For example, the pharmaceutically acceptable carrier can comprise one or more reagents selected from the group consisting of solvent, buffer, emulsifier, suspending agent, decomposer, disintegrating agent, dispersing agent, binding agent, excipient, stabilizing agent, chelating agent, diluent, gelling agent, preservative, wetting agent, lubricant, absorption delaying agent, liposome, and the like. The selection and quantity of these reagents falls within the professional literacy and routine technology of those skilled in the art.

According to the present invention, the pharmaceutically acceptable carrier comprises a solvent selected from the group consisting of water, normal saline, phosphate buffered saline (PBS), aqueous solution containing alcohol, and combinations thereof.

According to the present invention, the statistical analysis used in the following examples is performed by Student's t-test and Mann-Whitney U-test, and the p-value less than 0.05 is considered to be statistically significant.

Example 1

Preparation and Characteristics of Nanoparticles of Present Invention

FIG. 1A is a process flow diagram showing the preparation of the nanoparticles of the present invention. First, ascorbic acid (Sigma Aldrich) was used to reduce potassium permanganate ($KMnO_4$)(fisher scientific, Waltham, Mass.) to synthesize a core containing manganese dioxide, while a negatively charged lipid 1,2-dioleoyl-sn-glycero-3-phosphate (DOPA)(Avanti Polar Lipids, Alabaster) was used to coat the core. Briefly, two kinds of microemulsions (3 mL each), one contained DOPA lipid and KMnO4, another contained ascorbic acid, were prepared separately. To prepare the $Mn^{7+}$-loaded microemulsions, 74 μL of 35 mM DOPA and 40 μL of 300 mM KMnO4 were dropped to the oil phase of cyclohexane and Igepal-520 (7:3, v/v). To prepare the ascorbic acid buffer-loaded microemulsions, 100 μL of 250 mM ascorbic acid and 900 μL of 1 M NaOH were mixed as ten times ascorbic acid buffer acting as reducing agent, and 40 μL of ascorbic acid buffer were added into to the oil phase of cyclohexane and Igepal-520 (7:3, v/v). Two different kinds of microemulsions were mixed separately using a magnetic stir bar and plate for 10 minutes at room temperature. The emulsions were then mixed together and stirred for 40 minutes to form the condensed DOPA-coated $MnO_2$ cores. Next, 6 mL of 100% ethanol (Sigma Aldrich, St. Louis, Mo.) was added to disrupt the emulsion, and the mixture was centrifuged at 20,133 g for 15 minutes. After removing the supernatant solution, the precipitated $MnO_2$ cores were washed twice with 100% ethanol to remove the organic solvents with emulsifying agents, so that DOPA would surround the $MnO_2$ cores by hydrophilicity and phosphate coordination (with manganese). After the removal of ethanol, the precipitate was then resuspended in 400 μL of tetrahydrofuran (THF)(Sigma Aldrich, St. Louis, Mo.).

To formulate a drug-loadable nanoparticle, poly D,L-lactide-co-glycolic acid (PLGA)(50/50, inherent viscosity: 0.17 dl/g)(Green Square Materials Incorporation, Taoyuan, Taiwan) was used to carry Sorafenib and the core. D-α-Tocopherol polyethylene glycol 1000 succinate (TPGS) (Sigma Aldrich, St. Louis, Mo.) and other free lipids including 1,2-Dioleoyl-sn-glycero-3-phophocholine (DOPC), cholesterol, DSPE-PEG (2000) and DSPE-PEG Mal (Avanti Polar Lipids, Alabaster, Ala.) were used to stabilize the structure of the nanoparticles. That is, the $MnO_2$ cores were subjected to a multiple phase emulsion reaction. Briefly, an organic phase mixture of 11.49 μL of free lipids (molar ratio=DOPC:DSPE-PEG2000:DSPE-PEG2000 Mal:cholesterol=10:4:1:2), 5 μL of 150 mg/mL PLGA, and 2.5 μL of 132 mM TPGS dissolved in THF was mixed with 50 μL of MnO2 cores (molar ratio of total free lipids to DOPA=1:2) and then the whole organic phase was added dropwise into water phase contained 0.25% (w/v) PVA (volume ratio of organic phase:water phase=1:8) under stirring with magnetic stir bar and plate for 10 minutes at room temperature. After oil in water emulsification, the nanoparticles were formed by the self-assembly and the solution was sonicated for 3 minutes using Q125 sonicator (Qsonica, Newtown, Conn.) following by 2 h gentle stirring.

To deliver Sorafenib and manganese dioxide to liver cancer cells, the SP94 peptide targeting liver cancer cells (SFSIIHTPILPL with the amino acid sequence of SEQ ID No: 1) synthesized and purified (96% purity) by Kelowna International Scientific Inc. (Taipei, Taiwan) was conjugated with DSPE-PEG Mal on the surface of the nanoparticles. Briefly, the SP94 peptide was reduced using immobilized TCEP disulfide-reducing gel (Thermo Fisher Scientific, USA) according to the manufacturer's suggestion. SP94 peptides were then added into nanoparticles solution where they would react with DSPE-PEG Mal on the surface of the nanoparticles. Thereafter, the solution was centrifuged at 25,001 g for 30 minutes at room temperature, and the nanoparticles were then resuspended in water to obtain nanoparticles containing SP94 peptides and $MnO_2$ cores (i.e., SP94 PMD NPs) for further characterization, experiment or treatment. To synthesize nanoparticles containing SP94 peptides, Sorafenib and $MnO_2$ cores (i.e., SP94 PMDsor NPs), same procedure was used and 37.5 μL of 3.14 mM Sorafenib dissolved in THF was added in the organic phase.

Figure 1B:
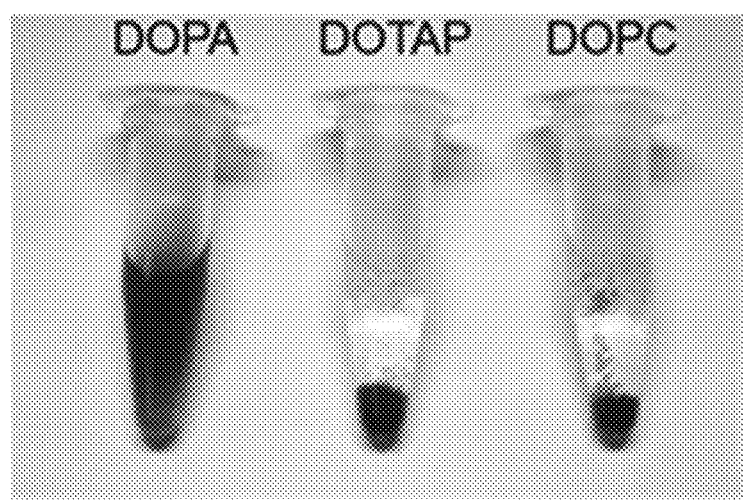
FIG. 1B is a photograph showing the appearance of the nanoparticles of the present invention.

FIG. 1B is a photograph showing the appearance of the nanoparticles of the present invention. As shown in FIG. 1B, only the negatively charged lipid DOPA can successfully prevent the cores from aggregation during synthesis of nanoparticles other than the positively charged lipid 1,2-dioleoyl-3-trimethylammonium-propane (DOTAP) or the neutral lipid 1,2-Dioleoyl-sn-glycero-3-phophocholine (DOPC). Therefore, the $MnO_2$ cores can be stabilized by the DOPA lipid and maintain good dispersity for long time.

The characteristic analysis of the nanoparticles (NPs) of the present invention, the particle size and surface charge were measured using a Zetasizer (3000HS, Malvern Instruments Ltd., Worcestershire, UK) at room temperature. The X-ray photoelectron spectroscopy (XPS) samples were prepared by adding the cores of the present invention onto amino silane-coated silica chip and then analyzed by National Nano Device Laboratories (Hsinchu, Taiwan). The size and geometries of the NPs were analyzed by transmission electron microscopy (TEM; JEM2010, JEOL, Tokyo, Japan). The NPs were dried on formvar-coated 100-mesh copper grids in a vacuum chamber at room temperature for two days prior to imaging. The drug encapsulation efficiency of the nanoparticles containing Sorafenib and $MnO_2$ cores (i.e., PMDsor NPs) was analyzed using a UV spectrophotometer (Multiskan, Thermo, USA) at 270 nm after the centrifugation. The absorbance of the supernatant of PMDsor NPs was subtracted with the absorbance of the supernatant of the nanoparticles containing no Sorafenib (i.e., PMD NPs) to get the percentage of unencapsulated Sorafenib. Finally, the encapsulation efficiency can be calculated using the regression line of different concentrations of Sorafenib.

Figure 1C:
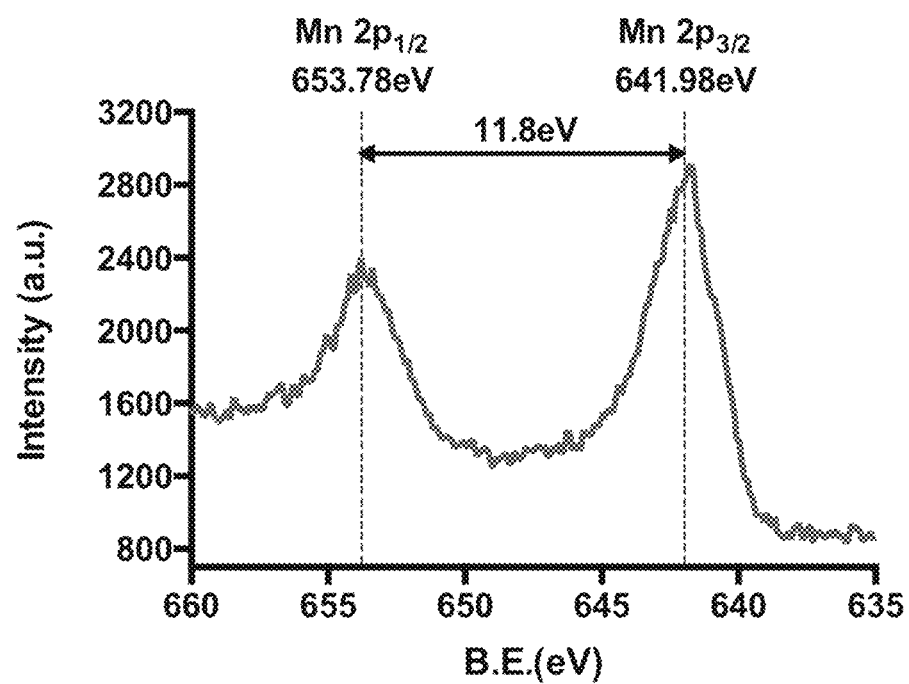
FIG. 1C is a schematic diagram showing the analysis of core components of the nanoparticles of the present invention using X-ray photoelectron spectroscopy (XPS).
Figure 1D:
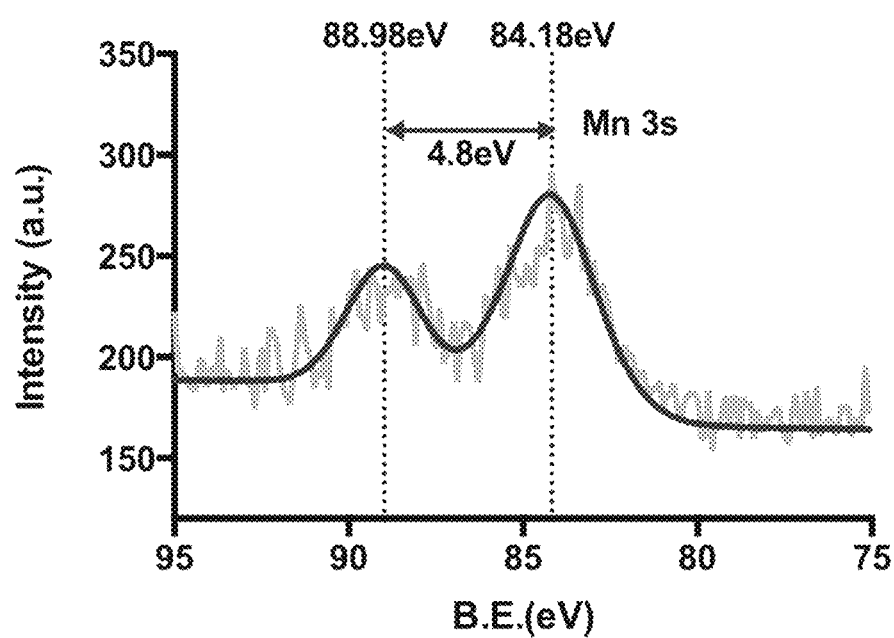
FIG. 1D is another schematic diagram showing the analysis of core components of the nanoparticles of the present invention using X-ray photoelectron spectroscopy.

FIG. 1C and FIG. 1D are schematic diagrams showing the analysis of core components of the nanoparticles of the present invention using X-ray photoelectron spectroscopy (XPS). As shown in FIG. 1C and FIG. 1D, the component of the cores was $MnO_2$ since the XPS peaks assigned to Mn $(2p_{1/2})$ and Mn $(2p_{3/2})$ at the binding energy (B.E.) of 653.78 and 641.98 eV respectively and peaks assigned to Mn (3s) at the binding energy (B.E.) of 88.98 and 84.18 eV. These detected XPS peaks of the cores are consistent with the ones of $MnO_2$, and thus proving the cores were made up of $MnO_2$.

Figure 2A:
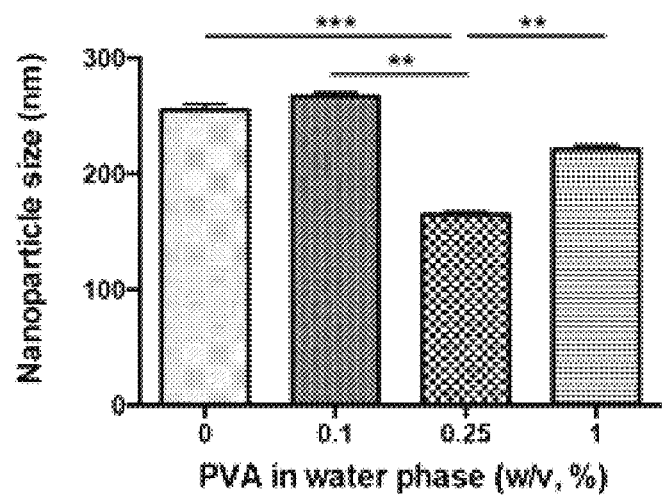
FIG. 2A is a schematic diagram showing the effect of the amount of PVA in water phase on the size of the nanoparticles, wherein "" indicates $p<0.01$; "*" indicates $p<0.001$.
Figure 2B:
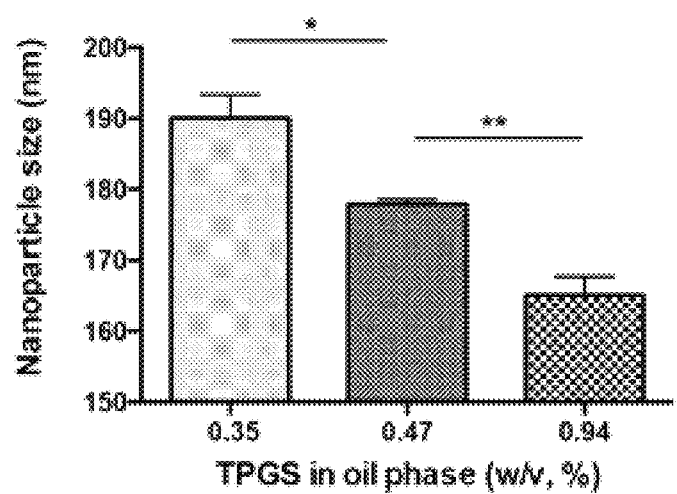
FIG. 2B is a schematic diagram showing the effect of the amount of TPGS in oil phase on the size of the nanoparticles, wherein "*" indicates $p<0.05$; "**" indicates $p<0.01$.

In the step of oil in water emulsification, the strategy using a co-surfactant, D-α-tocopherol polyethylene glycol 1000 succinate (TPGS) in oil phase and polyvinyl alcohol (PVA)(Sigma Aldrich, St. Louis, Mo.) in water phase was utilized to control the sizes of PLGA-based NPs. By this way, smaller droplets of microemulsions could be formed due to the reduction of surface tension and their sizes might further affect the drug release. Herein, the effects of the amount of emulsifiers, TPGS and PVA, on the size of PLGA-based NPs were investigated. FIG. 2A is a schematic diagram showing the effect of the amount of PVA in water phase on the size of the nanoparticles. As shown in FIG. 2A, there was a decrease in particle size, from 255 nm to 165 nm, when the concentration of PVA in water phase was increased from 0% to 0.25% (w/v) while the concentration of TPGS in oil phase fixed to 0.94% (w/v). FIG. 2B is a schematic diagram showing the effect of the amount of TPGS in oil phase on the size of the nanoparticles. As shown in FIG. 2B, there was either a decrease in particle size, from 190 to 165 nm, when the concentration of TPGS in oil phase was increased from 0.35% to 0.94% (w/v) while the concentration of PVA in water phase fixed to 0.25% (w/v).

Figure 2C:
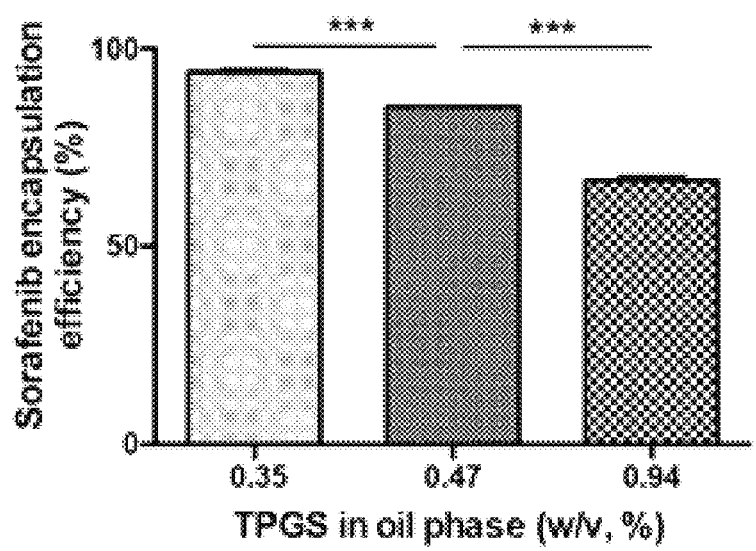
FIG. 2C is a schematic diagram showing the effect of the content of TPGS on the encapsulation efficiency of Sorafenib in the PLGA-based NPs containing Sorafenib (Psor), wherein "***" indicates $p<0.001$.

FIG. 2C is a schematic diagram showing the effect of the content of TPGS on the encapsulation efficiency of Sorafenib in the PLGA-based NPs containing Sorafenib (Psor). As shown in FIG. 2C, there was significant decline in Sorafenib encapsulation efficiency with increasing concentration of TPGS from 0.35% to 0.94% (w/v).

Figure 2D:
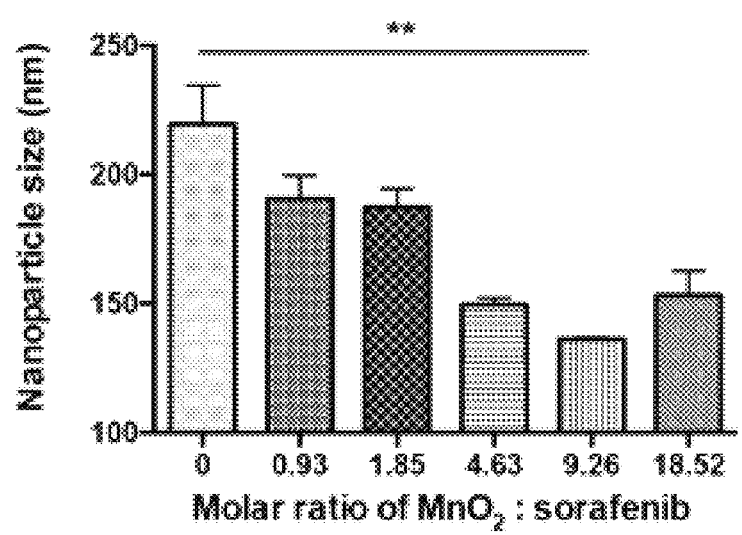
FIG. 2D is a schematic diagram showing the effect of different ratios of Sorafenib and manganese dioxide on the size of the nanoparticles, wherein "**" indicates $p<0.01$.
Figure 2E:
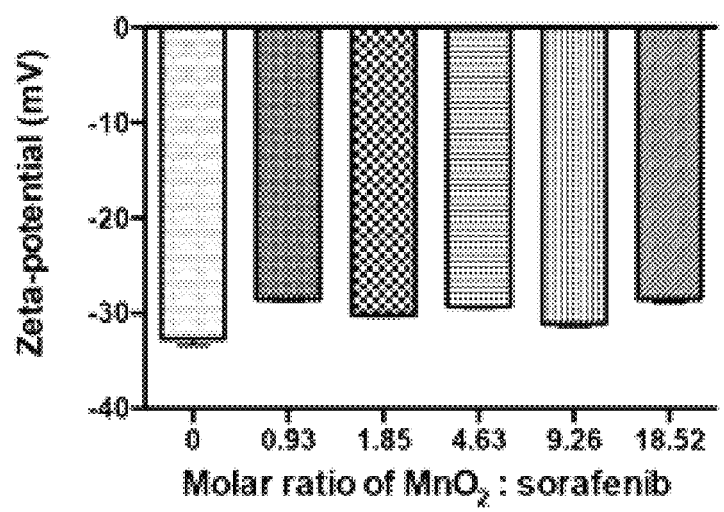
FIG. 2E is a schematic diagram showing the effect of different ratios of Sorafenib and manganese dioxide on zeta-potential.
Figure 2F:
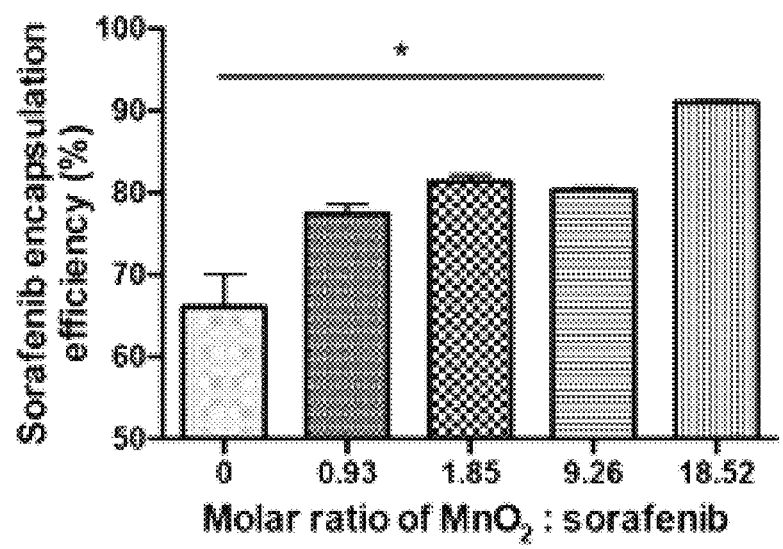
FIG. 2F is a schematic diagram showing the effect of different ratios of Sorafenib and manganese dioxide on the encapsulation efficiency of Sorafenib, wherein "*" indicates $p<0.05$.

In order to achieve the efficient co-delivery of Sorafenib as well as $MnO_2$ cores, the effects of different ratios of Sorafenib and manganese dioxide on the size of the nanoparticles, zeta-potential and encapsulation efficiency of Sorafenib were explored, and the results are shown in FIGS. 2D to 2F. As shown in FIG. 2D and FIG. 2F, an increase in the amount of $MnO_2$ cores neither competed the space for drug encapsulation inside PMDsor NPs nor enlarged nanoparticle size. The NPs even became smaller and the encapsulation efficiency went higher when more $MnO_2$ cores were added into oil phase (molar ratio of $MnO_2$ to Sorafenib, from 0 to 9.26) with fixed amount of Sorafenib. As shown in FIG. 2E, the zeta-potential of the NPs was not affected by an increased $MnO_2$ cores (around −30 mV), inferring that the negatively charged DOPA was more likely staying inside with $MnO_2$ rather than coming out to the surface of the PMDsor NPs. To optimize PMDsor NPs with the desired size and encapsulation efficiency, a molar ratio of 9.26 ($MnO_2$/Sorafenib), a concentration of 0.25% PVA and 0.47% TPGS were selected for the synthetic process.

Table 1 shows the physical properties (including size, polydispersity indexes (PDIs) and zeta-potentials) and encapsulation efficiency of the nanoparticles of the present invention. As shown in Table 1, the average diameters of finalized formulation of PMDsor NPs were 136.21±0.95 nm, with polydispersity indexes (PDIs) of 0.172±0.025, and the percentage of encapsulated Sorafenib was about 80%.

TABLE 1

| Size (nm) | PDI | Zeta-potential (mV) | Encapsulation Efficiency (%) |
|---|---|---|---|
| 136.21 ± 0.95 | 0.172 ± 0.025 | −31.13 ± 0.40 | 80.30 ± 0.52 |

Figure 2G:
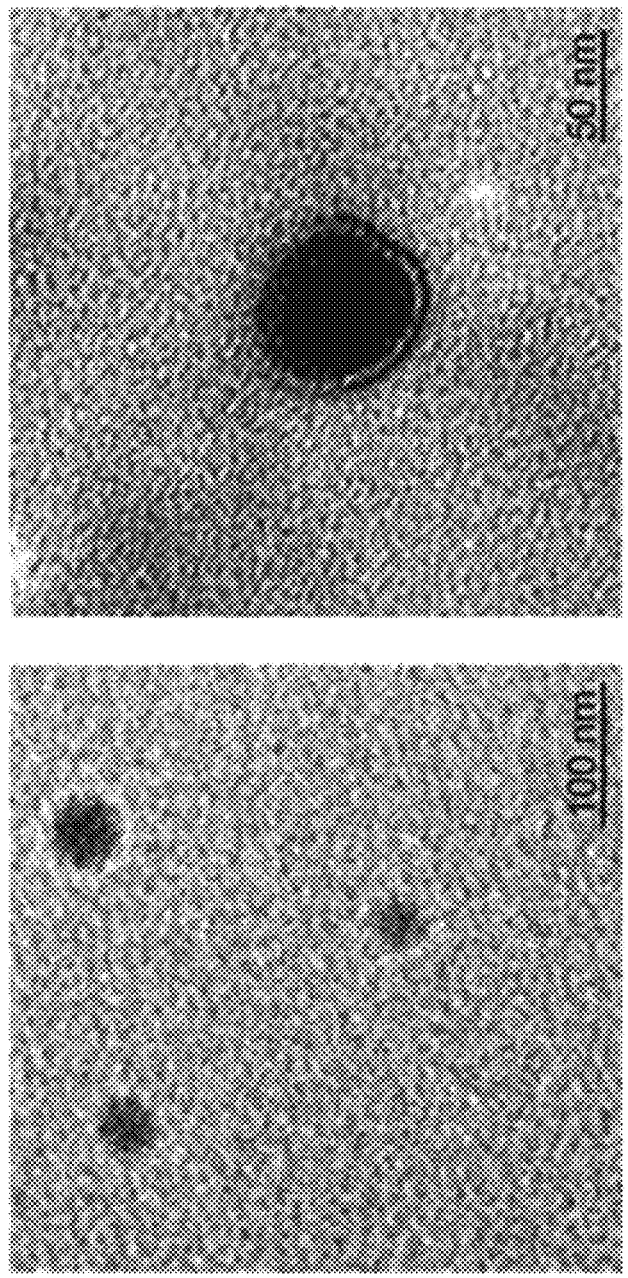
FIG. 2G is an image drawing showing the appearance and size distribution of the nanoparticles of the present invention using transmission electron microscopy (TEM).

In addition, the morphology and size distribution of PMDsor NPs were observed by transmission electron microscopy (TEM), and the result is shown in FIG. 2G As shown in FIG. 2G, PMDsor NPs were well-distributed spheres and the particle sizes are approximately 100 nm.

Example 2 pH-Dependent Reactivity, Drug Release Profiles and Oxygen Generation Effect of Nanoparticles of Present Invention Oxidative stress caused by tumor growth can significantly increase the concentration of $H_2O_2$ in the tumor microenvironment. In order to utilize the endogenous $H_2O_2$ produced by cancer cells and generate $O_2$ in situ, the $MnO_2$ cores must be delivered to the tumor region.

The reactivity of the PMD NPs toward $H_2O_2$ was then investigated by observing $H_2O_2$ quenching and $O_2$ generation. Herein, a PeroXOquant assay kit (Pierce, USA) was used to study if PMD NPs would be able to quench $H_2O_2$ with pH-dependent reactivity. For the quenching experiment, PMD NPs (750 μM) or vehicle NPs (without $MnO_2$ cores) were placed in $Na_2HPO_4$—$NaH_2PO_4$ buffer at pH 5.5 or 7.4, and $H_2O_2$ (300 μM) was added to initiate the reaction. The residual amount of $H_2O_2$ was determined over time using the PeroXOquant assay kit. The result is shown in FIG. 3A.

Figure 3A:
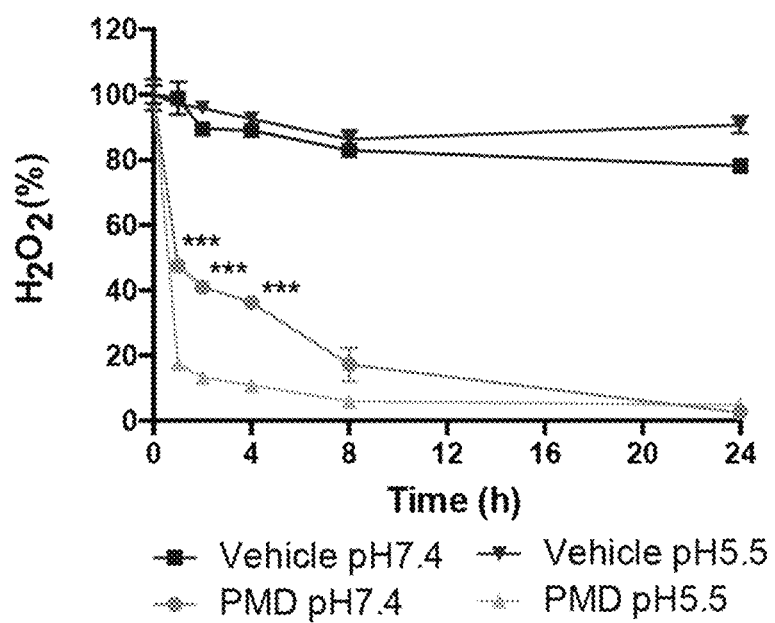
FIG. 3A is a schematic diagram showing the quenching of $H_2O_2$ by the nanoparticles of the present invention with pH-dependent reactivity, wherein the concentration of $H_2O_2$ is 300 μM, and the concentration of manganese dioxide is 750 μM; wherein "***" indicates $p<0.001$.

FIG. 3A is a schematic diagram showing the quenching of $H_2O_2$ by the nanoparticles of the present invention with pH-dependent reactivity. As shown in FIG. 3A, 300 μM of $H_2O_2$ could be completely quenched by 750 μM of $MnO_2$ in the solution at two different pH values (pH 5.5 and pH 7.4) after 24 hours. The PMD NPs thus have long-term quenching effect.

The cumulative release of Sorafenib from PMDsor NPs in the solutions at different pH values with or without 500 μM $H_2O_2$ was continuously observed for several time points. The release profiles of Sorafenib from PMDsor NPs were investigated in PBS buffer (pH 7.4) and acetic acid buffer (pH5.5) with or without $H_2O_2$ at 37° C. Briefly, Sorafenib-loaded NPs were put into centrifuge tubes and dispersed in 1 mL of buffer with or without $H_2O_2$ (500 μM). The tubes were put in an orbital shaker incubator and vibrated at 150 rpm at 37° C. At the designed time points after incubation, PMDsor NPs were centrifuged at 25,001 g for 30 minutes at 25° C. The pellets were then dissolved in 100 μL of dimethylsulfoxide (DMSO) and following by centrifugation at 25,001 g for 30 min at 25° C. again to remove the pellet. The supernatant with sorafenib was analyzed by a UV spectrophotometer at 270 nm. Finally, the drug release percentage can be calculated using the regression line of Sorafenib. The result is shown in FIG. 3B.

Figure 3B:
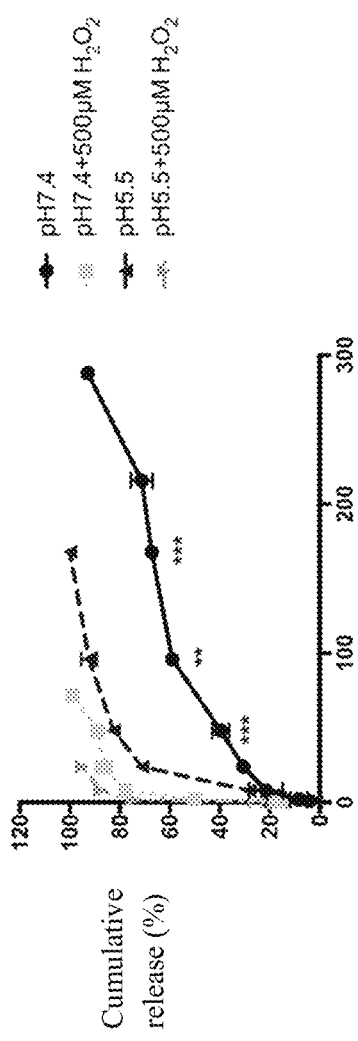
FIG. 3B is a schematic diagram showing the drug release behaviors of the nanoparticles of the present invention, wherein "" indicates $p<0.01$, and "*" indicates $p<0.001$.

FIG. 3B is a schematic diagram showing the drug release behaviors of the nanoparticles of the present invention. As shown in FIG. 3B, compared with the solutions without adding $H_2O_2$, the release profiles of PMDsor NPs at pH 5.5 and pH 7.4 were both significantly promoted by the presence of $H_2O_2$. Moreover, the release of Sorafenib at pH 5.5 was also speeded up compared with pH 7.4, indicating that the nanoparticles of the present invention have better drug release efficiencies in the acidic environment, such as the tumor microenvironment.

Example 3

In Vitro Cellular Uptake and Efficacy of SP94-Conjugated NPs

The NPs modified with tumor targeting peptides SP94 are the suitable carrier for the $MnO_2$ cores. The cellular uptake of targeted or non-targeted PMD NPs in HCA-1 murine liver cancer cells (provided by Dr. Dan Duda) and Hep3B human liver cancer cells (purchased from the American Type Culture Collection (ATCC)) was measured.

Coumarin 6 (C6), a hydrophobic small molecule, was used as a fluorescent tracer in the PLGA-based NPs, formulated with a final weight ratio of C6 to PLGA as 1/150. HCA-1 or Hep3B cells ($1×10^4$ cells/mL) were seeded in the 12-well plates (Costar, Ill., USA) and incubated for 12 hours. The cells were then treated with C6-containing SP94 PMD (i.e., SP94 PLGA-based manganese dioxide (PMD)-C6 NPs) or C6-containing PMD NPs (i.e., PMD-C6 NPs), at 37° C. for 4 hours. After removing the medium in each well, the cells were washed with PBS and fixed with 4% paraformaldehyde for 10 minutes. After aspiration of paraformaldehyde, cells were washed with PBS and counterstained with DAPI (Vector Laboratories, Burlingame, Calif.). The HCA-1 and Hep3B uptake of C6 was examined and quantified using a confocal microscope (LSM-780, Carl Zeiss, Germany). The results are shown in FIG. 4A and FIG. 4B.

Figure 4A:
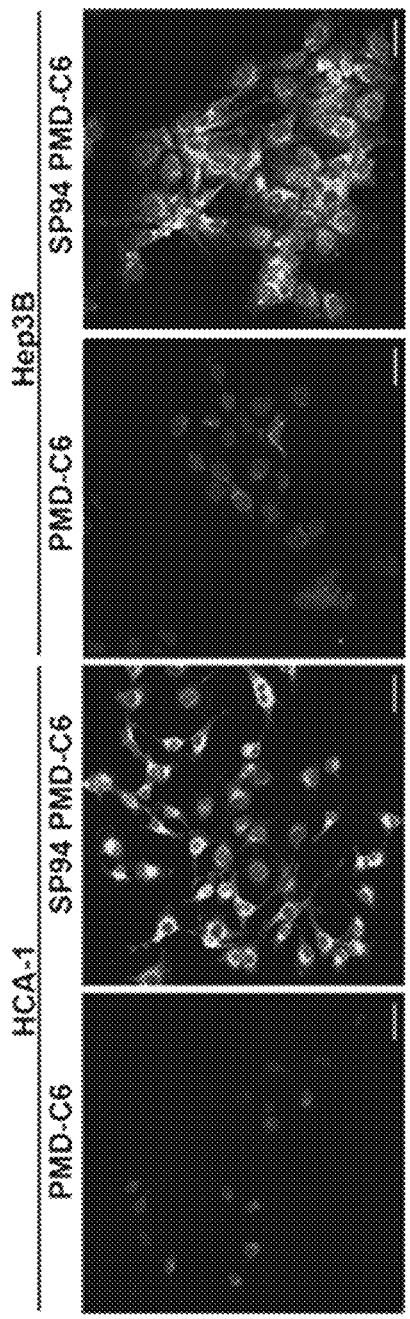
FIG. 4A is a dyed drawing showing in vitro cellular uptake of the nanoparticles of the present invention, wherein the green represents Coumarin 6 (C6); the blue represents the 4',6-diamidino-2-phenylindole (DAPI)-stained nuclei.
Figure 4B:
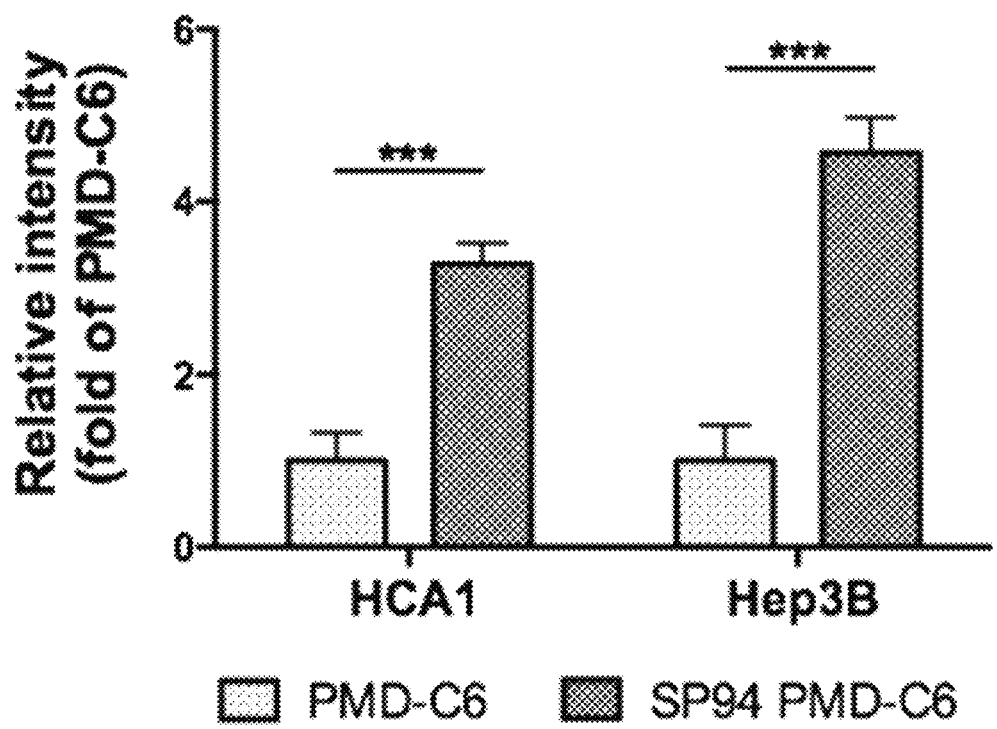
FIG. 4B is a schematic diagram showing in vitro cellular uptake of the nanoparticles of the present invention, wherein "***" indicates $p<0.001$.

FIG. 4A is a dyed drawing showing in vitro cellular uptake of the nanoparticles of the present invention. FIG. 4B is a schematic diagram showing in vitro cellular uptake of the nanoparticles of the present invention. As shown in FIG. 4A and FIG. 4B, all the NPs containing PLGA and $MnO_2$ cores (i.e., PMD NPs) were labeled with coumarin 6 (C6), a fluorescent molecule, and the cellular uptake of C6 was greater as being formulated in SP94 PMD-C6 NPs than PMD-C6 NPs after 4 h incubation.

Next, a Hypoxyprobe was used to test the hypoxia reduction ability of SP94 PMD NPs. The HCA-1 cells (5000 cells/well) were seeded on the coverslips in two 24-well plates (Costar, Ill.) one day before treatment. After treated with different concentrations of SP94 PMD NPs (0, 20, 80

μM), the PMD-treated plates were cultured under hypoxic condition (1% $O_2$) for 24 hours. The untreated plates were incubated under normoxic condition for 24 hours as control group. Then the plates were changed to serum free medium containing 0.5 μM pimonidazole hydrochloride (Hypoxyprobe, Burlington, Mass.) and put back into the incubators with previous conditions for 4 hours. The cells were washed with 0.5 mL PBS, then fixed with 4% paraformaldehyde at room temperature for 10 minutes. Washed twice with PBS to remove paraformaldehyde (Sigma Aldrich, St. Louis, Mo.), the cells were permeabilized with PBS containing 0.5% Triton X-100 at room temperature for 30 minutes. Washed three times with PBS, the coverslips were blocked with 5% BSA in PBS at room temperature for 1 hour. The cells were treated with anti-pimonidazole antibody (HP-FITC-Mab, 1:100 in 1% BSA/PBS) (Hypoxyprobe, Burlington, Mass.) and kept in dark at room temperature for 2 hours. Washed the coverslips five times with PBS, the nuclei were stained with DAPI (Vector Laboratories, Burlingame, Calif.). The immunocytochemistry was observed and quantified using a confocal microscope (LSM-780, Carl Zeiss, Germany) The results are shown in FIG. 4C and FIG. 4D.

Figure 4C:
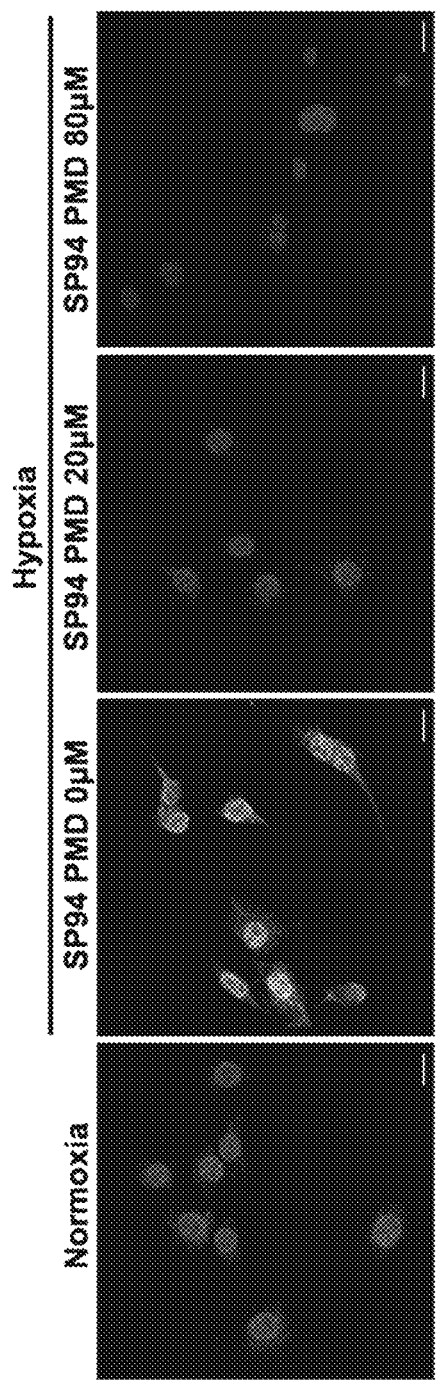
FIG. 4C is a dyed drawing showing the hypoxia reduction ability of the nanoparticles of the present invention in tumor cells.
Figure 4D:
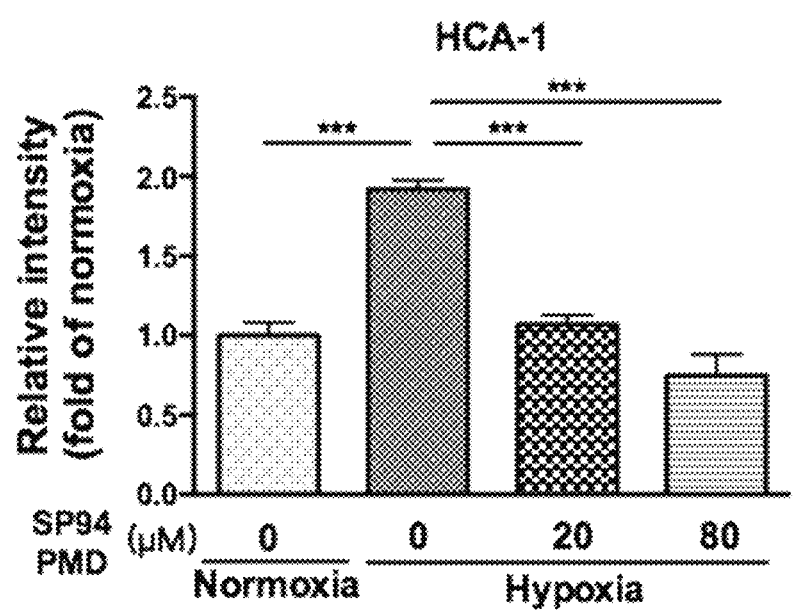
FIG. 4D is a schematic diagram showing the hypoxia reduction ability of the nanoparticles of the present invention in tumor cells, wherein "***" indicates $p<0.001$.

FIG. 4C is a dyed drawing showing the hypoxia reduction ability of the nanoparticles of the present invention in tumor cells. FIG. 4D is a schematic diagram showing the hypoxia reduction ability of the nanoparticles of the present invention in tumor cells. As shown in FIG. 4C and FIG. 4D, as the cells were treated with SP94 PMD NPs, the hypoxic condition detected by anti-pimonidazole antibodies was significantly decreased (~2-fold decrease of fluorescence). The result indicated the successful production of $O_2$ by incubating SP94 PMD NPs with liver cancer cells under hypoxic stress.

To investigate the ability of SP94 PMDsor NPs in sensitizing HCC to Sorafenib and inhibiting cancer cells proliferation, murine liver cancer cell HCA-1 and human liver cancer cell JHH-7 (provided by Dr. Dan Duda) were treated with SP94 PMDsor NPs either under normoxia or hypoxia. The in vitro cell proliferation of the treatment using different nanoparticles (PLGA vehicles, SP94 PMD, PLGA vehicles containing Sorafenib (SP94 Psor), SP94 PMDsor) was simply examined by cell counting. According to a modified protocol, both JHH-7 and HCA-1 cells ($10^4$ cells per well) were seeded in two 12-well plates (Costar, Ill.), incubated for 12 hours and the plates would be either moved into the hypoxia incubator (1% $O_2$) or normoxia incubator. After 8 hours, cells would be trypsinized for counting (cell numbers of Day 0) or exposed to different nanoparticles. The number of cells would be counted for continuous 3 days (cell numbers of Day 1, 2, and 3), after the treatment of different nanoparticles in both hypoxia and normoxia. The results are shown in FIG. 4E and FIG. 4F.

Figure 4E:
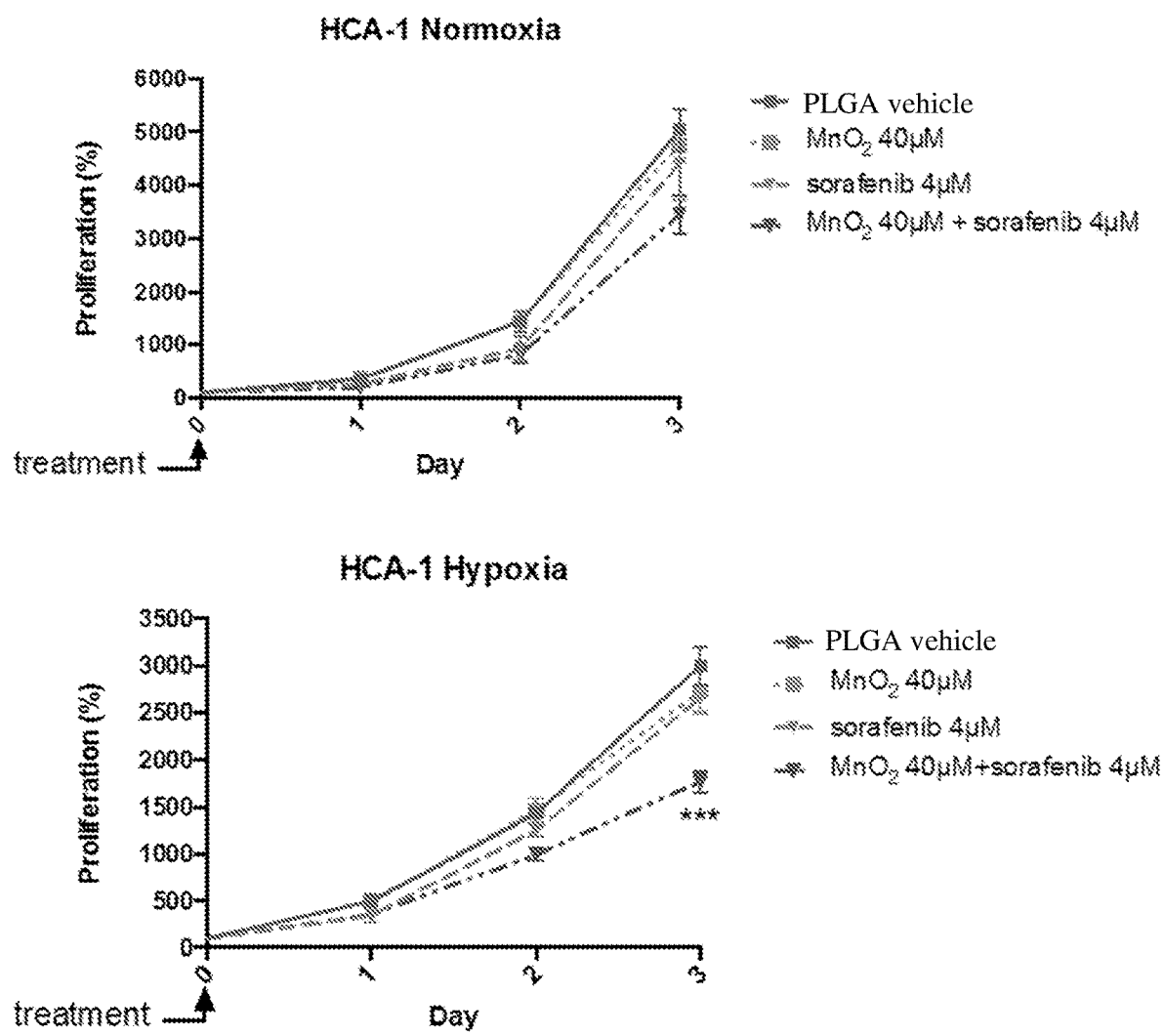
FIG. 4E is a schematic diagram showing the effect of the nanoparticles of the present invention on the proliferation of murine liver cancer cell HCA-1, wherein "***" indicates $p<0.001$.
Figure 4F:
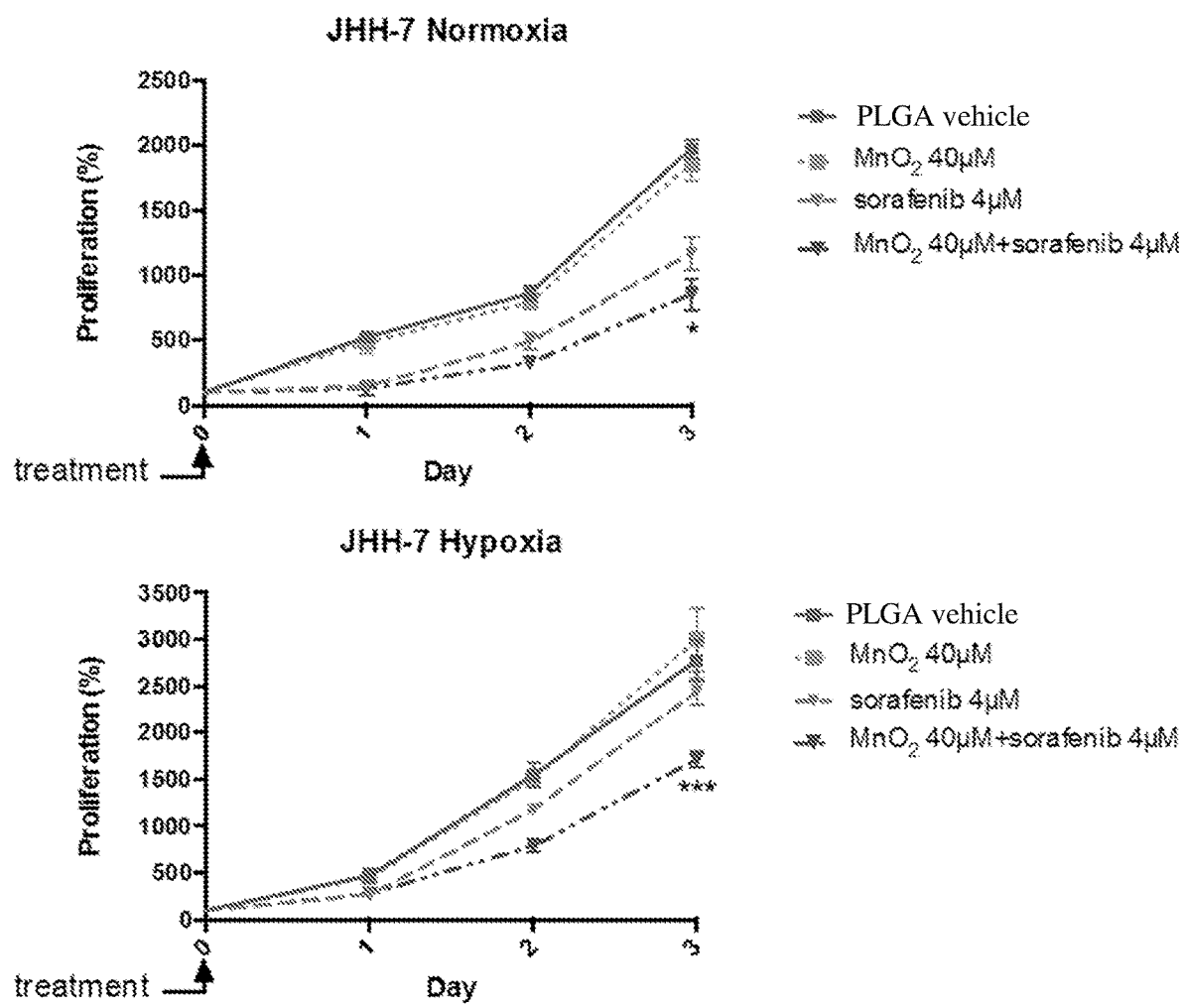
FIG. 4F is a schematic diagram showing the effect of the nanoparticles of the present invention on the proliferation of human liver cancer cell JHH-7, wherein "***" indicates $p<0.001$.

FIG. 4E is a schematic diagram showing the effect of the nanoparticles of the present invention on the proliferation of murine liver cancer cell HCA-1. FIG. 4F is a schematic diagram showing the effect of the nanoparticles of the present invention on the proliferation of human liver cancer cell JHH-7. As shown in FIG. 4E and FIG. 4F, Sorafenib-contained NPs (SP94 Psor) loses its ability to suppress cancer cell growth in both cell lines under hypoxia. However, SP94 PMDsor NPs simultaneously delivering $MnO_2$ cores and Sorafenib could significantly sensitize both JHH-7 and HCA-1 cells to Sorafenib under hypoxia. The result shows that the nanoparticles of the present invention can efficiently generate oxygen to ameliorate hypoxia-induced Sorafenib resistance of cancer cells and reduce the growth rates of cancer cells.

The in vitro cell viability of different formulations of NPs was examined using the MTT assay. HCA-1 and JHH-7 cells (1000 cells per well) were seeded in 96-well plates (Costar, Ill.), incubated for 12 hours and treated with different formulations (PLGA vehicles, SP94 PMD, SP94 Psor, SP94 PMDsor) in serum free medium. After 72 hours, 15 μL of 5 mg/mL MTT dissolved in PBS was added to each well and incubated for 3 hours at 37° C. The medium was aspirated, and 50 μL of DMSO was added to each well. The absorbance was measured using a UV spectrophotometer (Multiskan, Thermo, USA) at 570 nm. The results are shown in FIG. 4G and FIG. 4H.

Figure 4G:
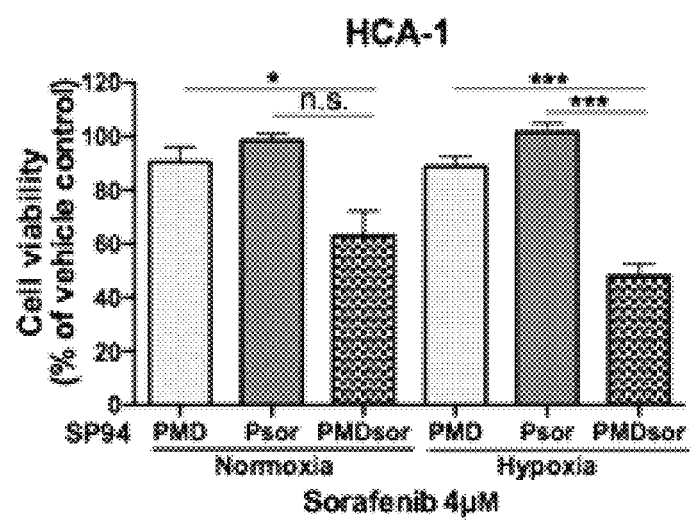
FIG. 4G is a schematic diagram showing the effect of the nanoparticles of the present invention on the viability of murine liver cancer cell HCA-1, wherein "*" indicates $p<0.05$; "***" indicates $p<0.001$.
Figure 4H:
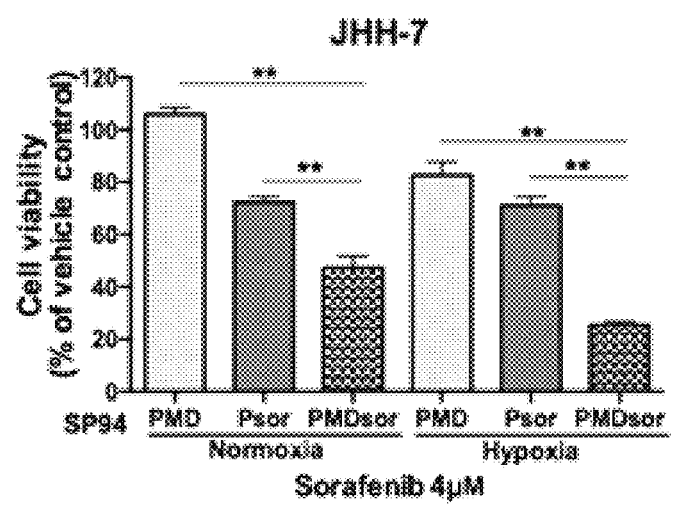
FIG. 4H is a schematic diagram showing the effect of the nanoparticles of the present invention on the viability of human liver cancer cell JHH-7, wherein "**" indicates $p<0.01$.

FIG. 4G is a schematic diagram showing the effect of the nanoparticles of the present invention on the viability of murine liver cancer cell HCA-1. FIG. 4H is a schematic diagram showing the effect of the nanoparticles of the present invention on the viability of human liver cancer cell JHH-7. As shown in FIG. 4G and FIG. 4H, in both relative Sorafenib-resistant cell line HCA-1 and Sorafenib-sensitive cell line JHH-7, SP94 PMDsor NPs could significantly sensitize the drug to cells under hypoxic condition compared with SP94 Psor NPs. The result demonstrated a synergistic effect is exerted when Sorafenib is co-delivered with the nanoparticles of the present invention. Hence, the nanoparticles of the present invention can not only effectively generate oxygen to alleviate tumor hypoxia, but also act as an agonist for enhancing effect of liver cancer drugs.

Example 4

Evaluation of Effect of Nanoparticles of Present Invention on Reversing Epithelial-Mesenchymal Transition (EMT) and Reducing Invasiveness of Liver Cancer Cells The epithelial-mesenchymal transition (EMT) has been recognized as an essential process to raise the invasiveness of tumor during the cancer progression of hepatocellular carcinoma (HCC). To examine whether SP94 PMD NPs could suppress the induction of EMT by hypoxia, quantitative real-time polymerase chain reaction (qRT-PCR) was used to quantify mRNA levels of EMT regulators (including Slug, Snail, Zeb2, and Twist1), epithelial markers (including E-cadherin and MTA3), and mesenchymal markers (including vimentin, fibronectin and N-cadherin), and glyceraldehyde 3-phosphate dehydrogenase (GAPDH) gene was used as an internal reference gene. HCA-1 ($1 \times 10^6$ cells) were seeded in two 12-well plates. After incubated for 12 hours, one plate would be moved into hypoxia incubator (1% $O_2$) and another plate would be kept in normoxia incubator as control group. After 8 hours, the cells in hypoxic condition were treated with different concentrations of SP94 PMD NPs (0, 20, 40 μM) and then incubated under hypoxia again for 48 hours. Total RNA was prepared with TRIzol reagent (Life Technologies, USA), and complementary DNA (cDNA) was reverse-transcribed with a High-Capacity cDNA Reverse Transcription Kit (Applied Biosystems, USA). PCR primer sequences are shown in the following Table 2. The cDNA from cells was amplified with specific primers with a PowerUp SYBR Green Master Mix (Applied Biosystems, USA) and a 7500 Real Time PCR System (Applied Biosystems, USA). The expression of mRNA of the target gene was evaluated by the comparative $C_T$ method.

TABLE 2

| Genes | Forward primers | Reverse primers |
|---|---|---|
| Cdh2 | 5'-AGCGCAGTCTTACCGA AGG-3' (SEQ ID No: 2) | 5'-TCGCTGCTTTCATACT GAACTTT-3' (SEQ ID No: 3) |
| Fn1 | 5'-TGTGACCAGCAACACG GTG-3' (SEQ ID No: 4) | 5'-ACAACAGGAGAGTAGG GCGC-3' (SEQ ID No: 5) |
| Vim | 5'-CTTGAACGGAAAGTGG AATCCT-3' (SEQ ID No: 6) | 5'-GTCAGGCTTGGAAACG TCC-3' (SEQ ID No: 7) |
| Cdh1 | 5'-CAGTCATAGGGAGCTG TCTACCAAA-3' (SEQ ID No: 8) | 5'-GGGTACACGCTGGGAA ACAT-3' (SEQ ID No: 9) |
| Mta3 | 5'-AAAAGCAGAAGCACCA GGAA-3' (SEQ ID No: 10) | 5'-GGCCCATCTAGACCAT TGTG-3' (SEQ ID No: 11) |
| Snai1 | 5'-CACACGCTGCCTTGTG TCT-3' (SEQ ID No: 12) | 5'-GGTCAGCAAAAGCACG GTT-3' (SEQ ID No: 13) |
| Snai2 | 5'-TGGTCAAGAAACATTT CAACGCC-3' (SEQ ID No: 14) | 5'-GGTGAGGATCTCTGGT TTTGGTA-3' (SEQ ID No: 15) |
| Zeb2 | 5'-ATTGCACATCAGACTT TGAGGAA-3' (SEQ ID No: 16) | 5'-ATAATGGCCGTGTCGC TTCG-3' (SEQ ID No: 17) |
| Twist1 | 5'-CTGCCCTCGGACAAGC TGAG-3' (SEQ ID No: 18) | 5'-CTAGTGGGACGCGGAC ATGG-3' (SEQ ID No: 19) |

Figure 5A:
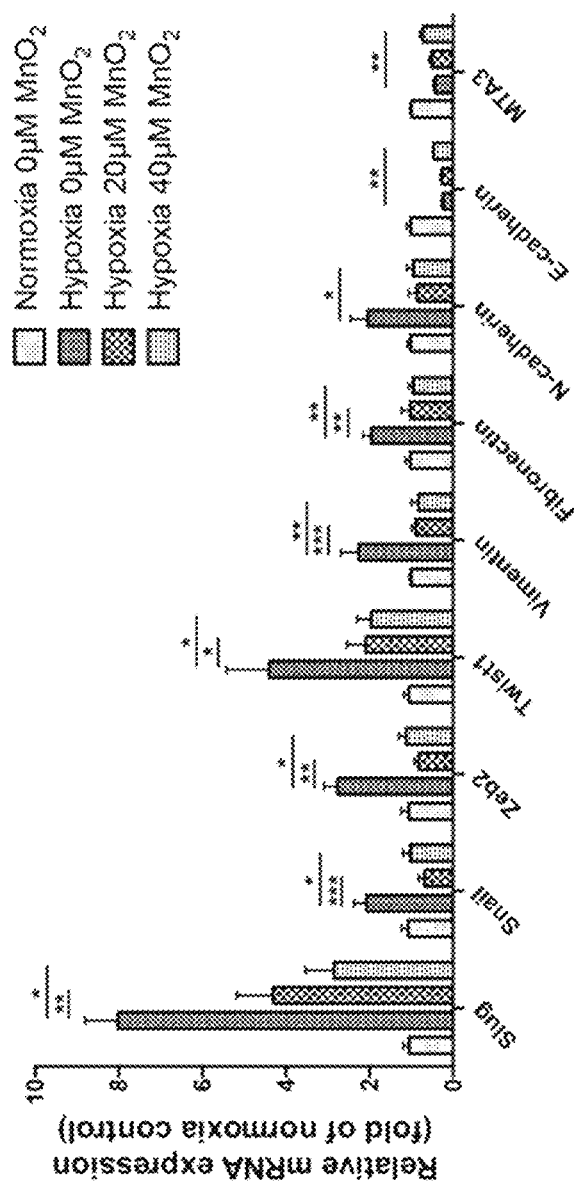
FIG. 5A is a schematic diagram showing the effect of the nanoparticles of the present invention on the mRNA levels of EMT regulators, epithelial markers, and mesenchymal markers, wherein "*" indicates $p<0.05$; "" indicates $p<0.01$; "*" indicates $p<0.001$.

FIG. 5A is a schematic diagram showing the effect of the nanoparticles of the present invention on the mRNA levels of EMT regulators, epithelial markers, and mesenchymal markers. As shown in FIG. 5A, expression of Slug, Snail, Zeb2, Twist1, Vimentin, Fibronectin, and N-cadherin significantly increased when HCA-1 cells were cultured in hypoxic condition. After the treatment of SP94 PMD NPs with two different concentrations (20 and 40 μM), the changes of these genes were reversed back and closer to normoxic level, indicating the inhibition of EMT. On the other hand, the mRNA levels of E-cadherin and MTA3 increased significantly with the treatment of 40 μM SP94 PMD NPs while HCA-1 cells were kept under hypoxia. These data indicated that induction of EMT in HCA-1 by hypoxia could be reversed by SP94 PMD NPs.

The invasiveness of cancer cells is related to metastasis, a main cause of death in cancer patients. To evaluate whether SP94 PMD NPs could reduce the invasiveness of HCA-1 under hypoxia, the transwell inserts from Millipore were used. HCA-1 cells were trypsinized and pelleted by centrifugation. Removed supernatant, then the cells were resuspended in serum free medium to prepare the suspension ($5\times10^5$ cells/mL). The cell suspension was added to the top of the filter membrane in a transwell insert (Millipore Corp., Billerica, Mass.). The upper chambers were added with different concentrations of SP94 PMD NPs (0, 20, 40 μM). Culture medium supplemented with 10% FBS was carefully added to the lower chamber in a 24-well plate (Costar, Ill.). The cells were incubated for 72 hours at 37° C. under the condition of hypoxia (1% $O_2$) and 5% $O_2$. The medium was removed, and the upper face of the membrane was washed with PBS twice and the remaining cells were carefully removed by cotton. The lower face of the membrane was then fixed with 4% paraformaldehyde at room temperature for 5 minutes. The paraformaldehyde was removed from the plates and the invaded cells were stained with 1% crystal violet (Sigma Aldrich, St. Louis, Mo.) in 90% ethanol for 30 minutes. The stained membrane was repeatedly soaked in fresh PBS to remove the crystal violet. The membrane was observed with the cell-migrated side up using an inverted microscope (IX83, OLYMPUS, Japan) and the number of cells in different fields were counted using Image J. The results are shown in FIG. 5B and FIG. 5C.

Figure 5B:
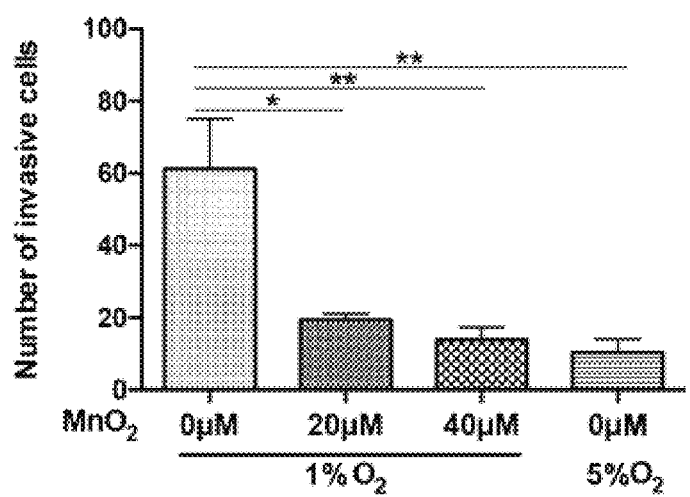
FIG. 5B is a schematic diagram showing the effect of the nanoparticles of the present invention on reducing the invasiveness of HCA-1 cells under hypoxia, wherein "*" indicates $p<0.05$; "**" indicates $p<0.01$.
Figure 5C:
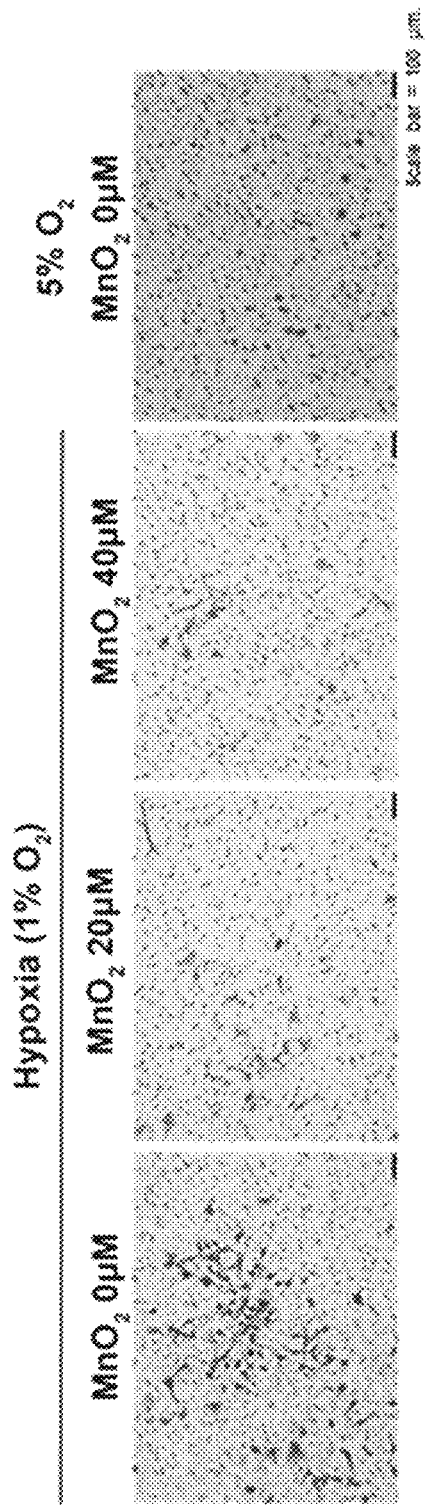
FIG. 5C is a cell staining drawing showing the effect of the nanoparticles of the present invention on reducing the invasiveness of HCA-1 cells under hypoxia.

FIG. 5B is a schematic diagram showing the effect of the nanoparticles of the present invention on reducing the invasiveness of HCA-1 cells under hypoxia. FIG. 5C is a cell staining drawing showing the effect of the nanoparticles of the present invention on reducing the invasiveness of HCA-1 cells under hypoxia. As shown in FIG. 5B and FIG. 5C, the number of invaded cells was quantified by directly counting in the pictures and there was at least 3-fold decrease in SP94 PMD NPs-treated cells invading toward the lower chamber compared with untreated cells within the 1% $O_2$ atmosphere. The results indicated that the hypoxic stress would enhance the invasiveness of HCA-1 cells and treatment with SP94 PMD NPs could significantly reduce the numbers of invaded cells.

Example 5

In Vitro and In Vivo MR Imaging of SP94 PMD NPs

It is known that $MnO_2$ nanoparticles were generally insoluble and remained stable at neutral pH. However, after being internalized by cells the particles could be degraded in the acidic organelle (endosome or lysosome) releasing $Mn^{2+}$ ions which are known to be potent T1 MRI contrast agents. For in vitro MRI, PMD NPs solution with different concentrations was prepared in pH 5.5 and pH 7.4 buffer added with 1 mM $H_2O_2$. The solutions were scanned under a 7T animal MRI scanner (Bruker, USA). The relaxation rates r1 (1/T1) under different pH values were calculated from T1 values at different Mn concentrations. The result is shown in FIG. 6A.

Figure 6A:
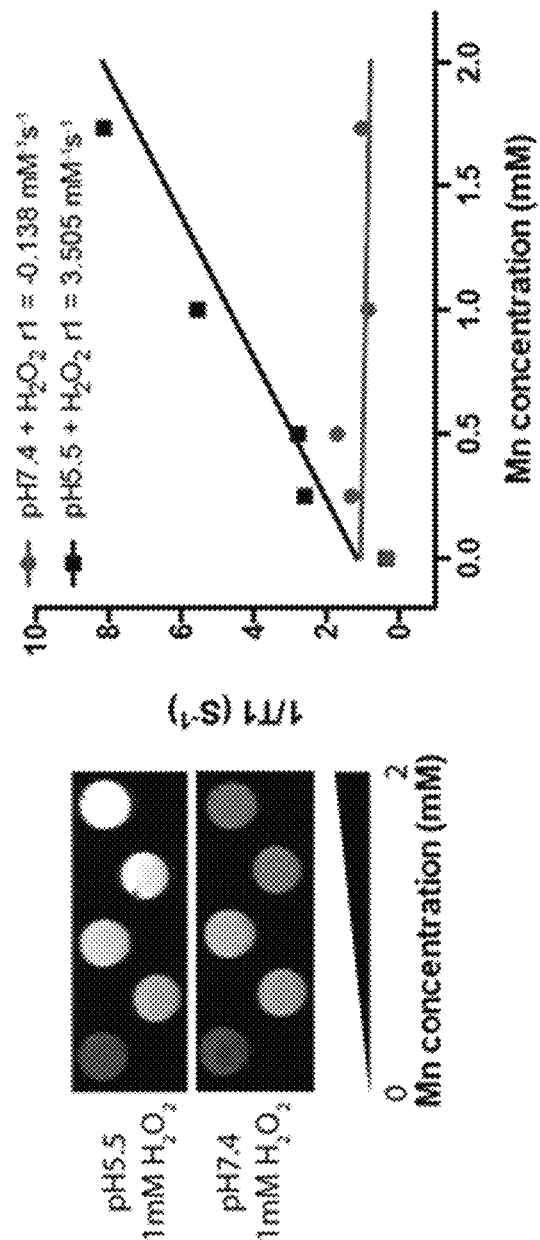
FIG. 6A is an in vitro MR imaging and schematic diagram of the nanoparticles of the present invention.

FIG. 6A is an in vitro MR imaging and schematic diagram of the nanoparticles of the present invention. As shown in FIG. 6A, T1 images of PMD NPs exhibited significant brightening effect in a concentration-dependent manner at pH 5.5, whereas the contrast effect in neutral condition was not detected. Furthermore, the relaxation rates r1 (1/T1) at pH 5.5 (3.505 $mM^{-1}s^{-1}$) was significant higher than r1 in neutral condition (−0.138 $mM^{-1}s^{-1}$), indicating the successful production of $Mn^{2+}$ ions.

For in vivo MRI, male C3H/HeNCrNarl (4-5 weeks old, 25 g) mice were purchased from the National Laboratory Animal Center (Taipei, Taiwan). HCA-1 cells were implanted heterotopically in the right legs via subcutaneous injection. The mice were conducted after 4 weeks of tumor growth. Animal care and use were performed in compliance with the 'Guide for the Care and Use of Laboratory Animals' prepared by the Institute of Laboratory Animal Resources, National Research Council, published by the National Academy Press. Animals were scanned by a 7T animal MRI scanner (Bruker, USA) before and after i.v. injection of SP94 PMD NPs at a dose of 20 mg/kg of $MnO_2$. The results are shown in FIG. 6B and FIG. 6C.

Figure 6B:
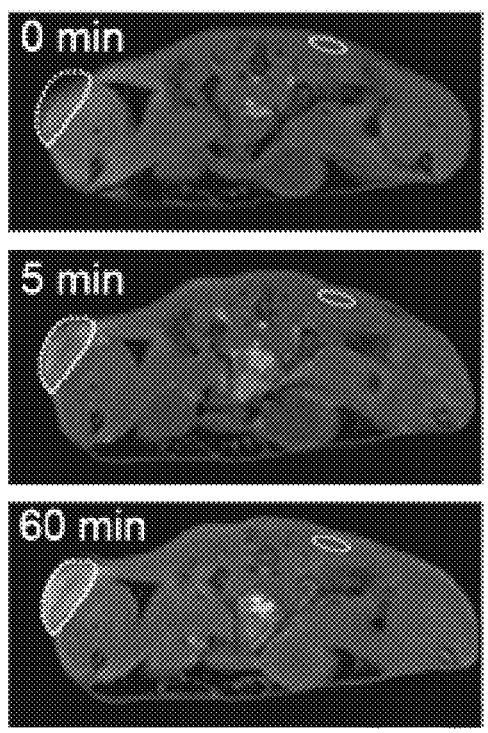
FIG. 6B is an in vivo MR imaging diagram of the nanoparticles of the present invention.
Figure 6C:
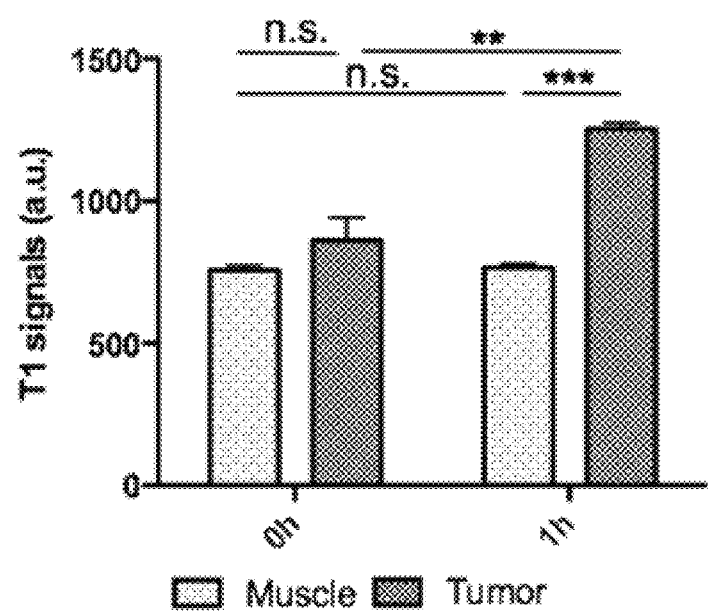
FIG. 6C is an in vivo MRI schematic diagram of the nanoparticles of the present invention, wherein n.s. indicates no significant difference; "" indicates $p<0.01$; "*" indicates $p<0.001$.

FIG. 6B is an in vivo MR imaging diagram of the nanoparticles of the present invention. FIG. 6C is an in vivo MRI schematic diagram of the nanoparticles of the present invention. As shown in FIG. 6B and FIG. 6C, the contrast enhancement caused by SP94 PMD NPs was observed at 5 minutes post injection. At 1 hour post injection of SP94 PMD NPs, the T1 signals of tumor enhanced 1.45 fold while the T1 signals of muscle showed no significant difference indicating successful delivery and decomposition of the $MnO_2$ cores in the tumor microenvironment. The result indicated that the nanoparticles of the present invention can be used as an MRI contrast agent, particularly in the tumor microenvironment.

Example 6

In Vivo Efficacy of Targeted SP94 PMDsor NPs

It is known that tumor microenvironment has the characteristics favoring the reaction between $MnO_2$ and $H_2O_2$ with the acidic pH and elevated levels of $H_2O_2$. Hence, the NPs containing $MnO_2$ might be able to generate oxygen and relieve tumor hypoxia by reacting with endogenous $H_2O_2$ produced by cancer cells. Sorafenib acting as an anti-angiogenesis drug can reduce blood vessels formation and reduce the supply of oxygen and nutrient in HCC. However, the anti-angiogenesis effect can lead to severe tumor hypoxia. Herein, both tumor hypoxia and blood vessels in different treatment groups by Hypoxyprobe and CD31 were investigated respectively. To establish orthotopic model for treatment, five-week-old male mice were implanted with HCA-1 cells ($2 \times 10^6$ cells) in a 20 μL Matrigel solution in their livers. The HCA-1 tumor bearing mice were treated ten days after implantation. HCA-1 tumor-bearing mice were treated with different formulations (SP94 PMD, SP94 Psor, and SP94 PMDsor NPs) at a dose of 5 mg/kg of Sorafenib and 10 mg/kg of $MnO_2$ by intravenous injection (three doses per week for 2 weeks). The therapeutic efficacy and the change of tumor microenvironments was analyzed after two weeks of treatment. The tumor volume was calculated with the following formula: volume=width×length×height/2. HCA-1 tumor bearing mice were treated as the treatment plan. At 6 hours post injection of the last dose of different formulations, tumors were excised 60 minutes after i.v. injection with pimonidazole hydrochloride (60 mg/kg) (Hypoxyprobe, Burlington, Mass.) and fixed with 4% PFA (in PBS) overnight. After fixation, tumors were dehydrated with 30% sucrose (Sigma Aldrich, St. Louis, Mo.) and embedded in OCT compound (Sakura Finetek USA, Inc., Torrance, Calif.). Frozen section (10 μm thick) for immunofluorescence staining were fixed in acetone at −20° C. for 10 minutes and washed with PBS. The sections were then blocked with 5% bovine serum albumin for 1 hour and incubated with anti-pimonidazole antibodies conjugated with FITC (1:100 in 1% BSA/PBS, Hypoxyprobe, Burlington, Mass.), and rabbit anti-CD31 mouse antibodies (1:100 in 1% BSA/PBS, abcam, England) at 4° C. After washed with PBS, the sections were further incubated with Alexa Fluor® 647 secondary anti-rabbit IgG antibodies (1:200 in 1% BSA/PBS, Thermo Fisher Scientific, USA) for 1 hour. Unbound secondary antibodies were washed away with PBS. Cell nuclei were counterstained with DAPI (Vector Laboratories, Burlingame, Calif.). The images were observed using a confocal microscope (LSM780, Zeiss, Germany). The results are shown in FIG. 7A to FIG. 7C.

Figure 7A:
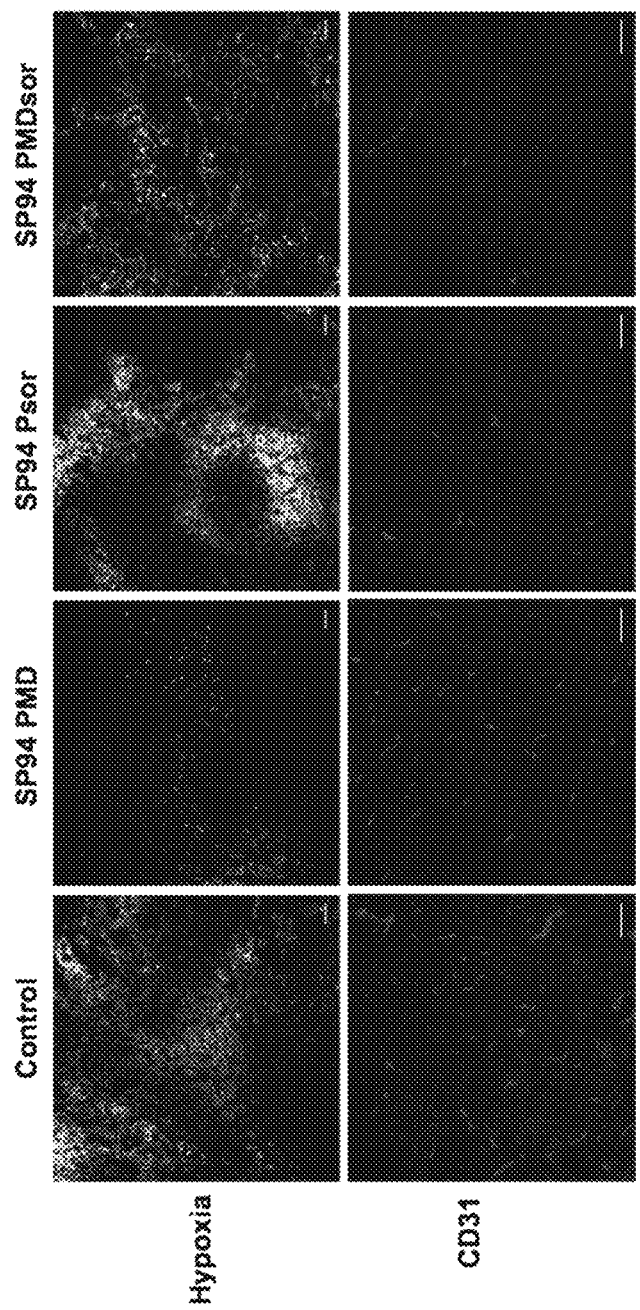
FIG. 7A is a fluorescent staining diagram of the effect of the nanoparticles of the present invention on ameliorating tumor hypoxia and angiogenesis, wherein the blue represents DAPI; the red represents CD31; the green represents anti-pimonidazole antibody; scale bar=50 μm.
Figure 7B:
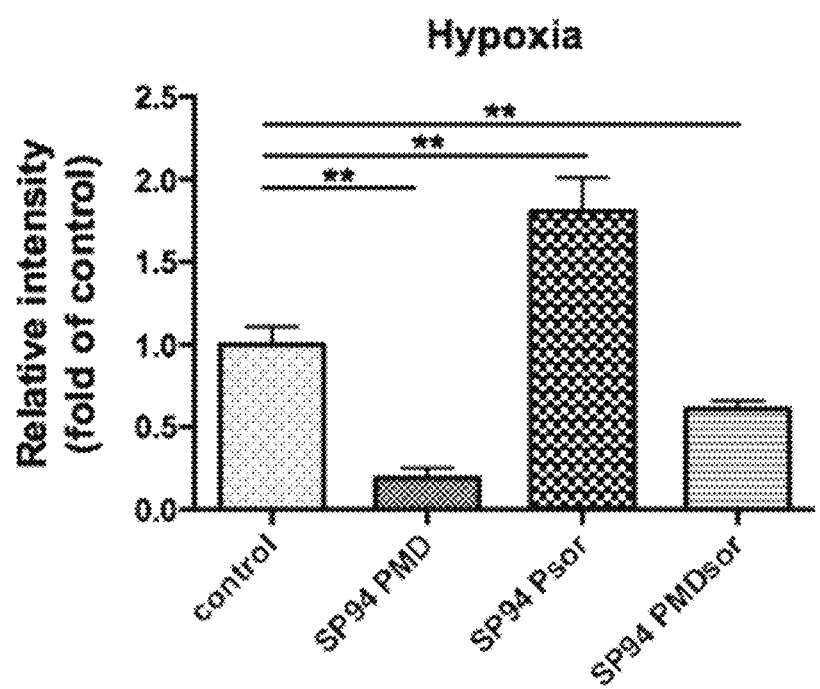
FIG. 7B is a schematic diagram showing the effect of the nanoparticles of the present invention on ameliorating tumor hypoxia, wherein "**" indicates $p<0.01$.
Figure 7C:
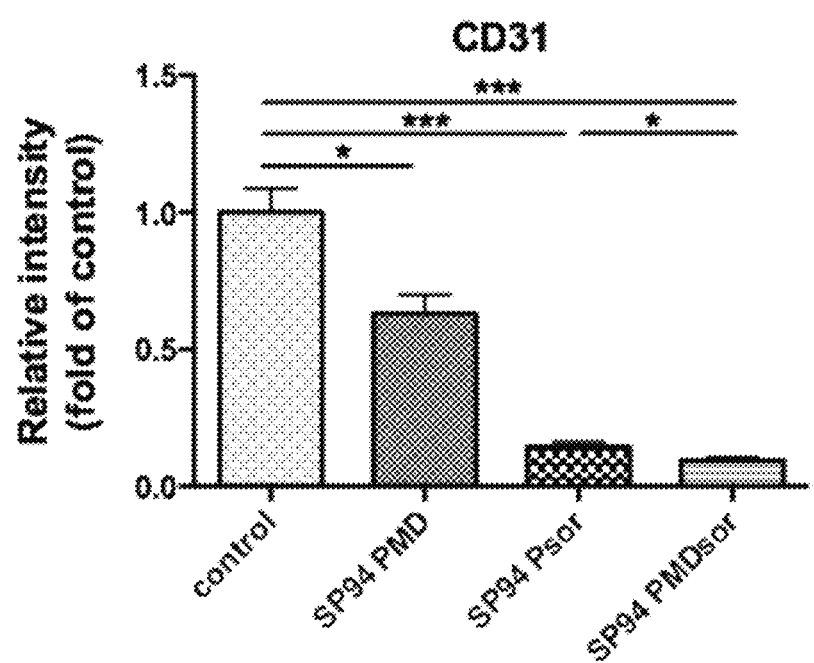
FIG. 7C is a schematic diagram showing the effect of the nanoparticles of the present invention on reducing angiogenesis, wherein "*" indicates $p<0.05$; "***" indicates $p<0.001$.

FIG. 7A is a fluorescent staining diagram of the effect of the nanoparticles of the present invention on ameliorating tumor hypoxia and angiogenesis. FIG. 7B is a schematic diagram showing the effect of the nanoparticles of the present invention on ameliorating tumor hypoxia. FIG. 7C is a schematic diagram showing the effect of the nanoparticles of the present invention on reducing angiogenesis. As shown in FIG. 7A and FIG. 7B, SP94 PMD and SP94 PMDsor NPs significantly reduced the green fluorescence compared with the control group, indicating the $MnO_2$ NPs could successfully reduce tumor hypoxia by triggering the decomposition of $H_2O_2$ and generation of $O_2$ in tumor. As shown in FIG. 7A to FIG. 7C, despite the significant reduction of blood vessels that were observed in tumor tissues after the treatment of SP94 Psor and SP94 PMDsor NPs, the hypoxic situation only became much more severe after administrating SP94 Psor NPs. In contrast, tumor hypoxia was attenuated to a lower level upon treatment with SP94 PMDsor NPs, indicating that adding $MnO_2$ cores to the Sorafenib-contained NPs can suppress the increased tumor hypoxia caused by Sorafenib. In addition, as shown in FIG. 7A and FIG. 7C, a significant decrease in blood vessels signals was observed while only treated with SP94 PMD NPs without drug loading. Therefore, SP94 PMD NPs might be able to inhibit angiogenesis by solving tumor hypoxia. Incorporation of $MnO_2$ cores to sorafenib-contained NPs suppressing the tumor hypoxia may result in enhanced anti-angiogenic therapy.

Figure 8A:
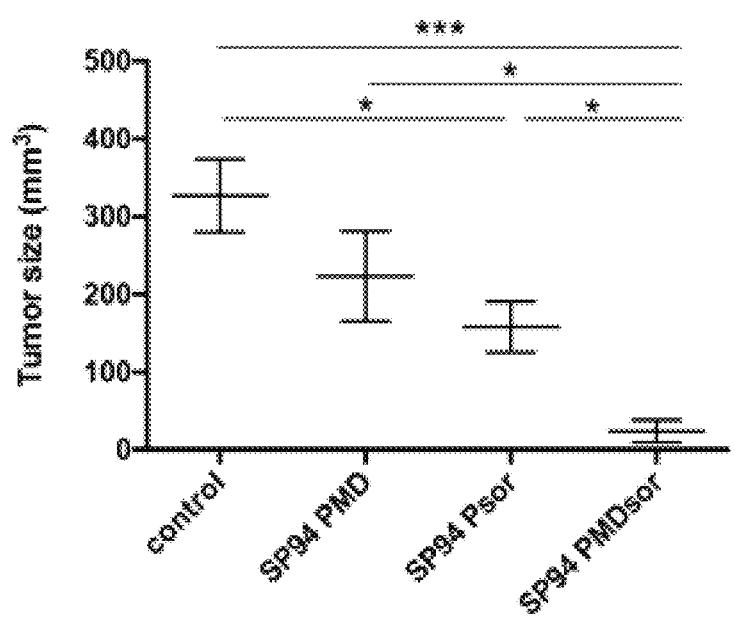
FIG. 8A is a schematic diagram showing the effect of the nanoparticles of the present invention on the growth of HCC, wherein "*" indicates $p<0.05$; "***" indicates $p<0.001$.

Next, the impact of HCC growth after treatment with SP94 PMDsor NPs was evaluated. The result is shown in FIG. 8A. FIG. 8A is a schematic diagram showing the effect of the nanoparticles of the present invention on the growth of HCC. As shown in FIG. 8A, co-delivery of Sorafenib and the $MnO_2$ cores by SP94 PMDsor NPs significantly inhibited the primary HCA-1 tumor growth. In contrast, SP94 Psor NPs only induced moderate tumor growth suppression and SP94 PMD NPs showed no significant tumor growth inhibition. In the orthotopic HCA-1 tumor model, spontaneous lung metastases happen and form detectable nodules approximately 4 weeks after tumor implantation. Herein, the lung tissues were also collected to observe the metastasis modulation. The lung tissue was cut into small pieces and fixed in 4% PFA (in PBS) overnight before being embedded in paraffin wax. The sections were then stained with hematoxylin and eosin (H&E) and observed with an inverted microscope (IX83, OLYMPUS, Japan). The results are shown in FIG. 8B and FIG. 8C.

Figure 8B:
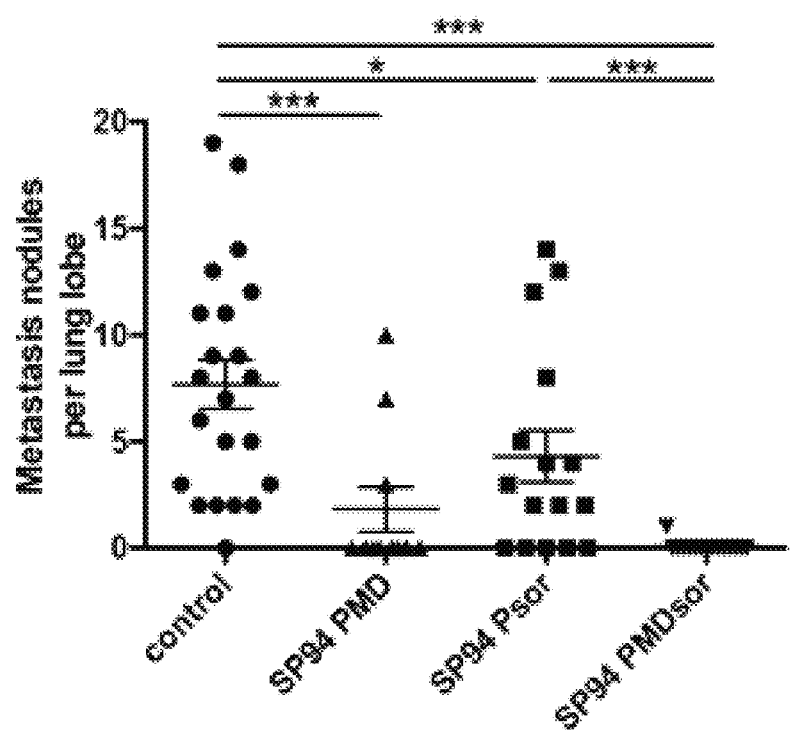
FIG. 8B is a schematic diagram showing the effect of the nanoparticles of the present invention on orthotopic tumor metastasis, wherein "*" indicates $p<0.05$; "***" indicates $p<0.001$.
Figure 8C:
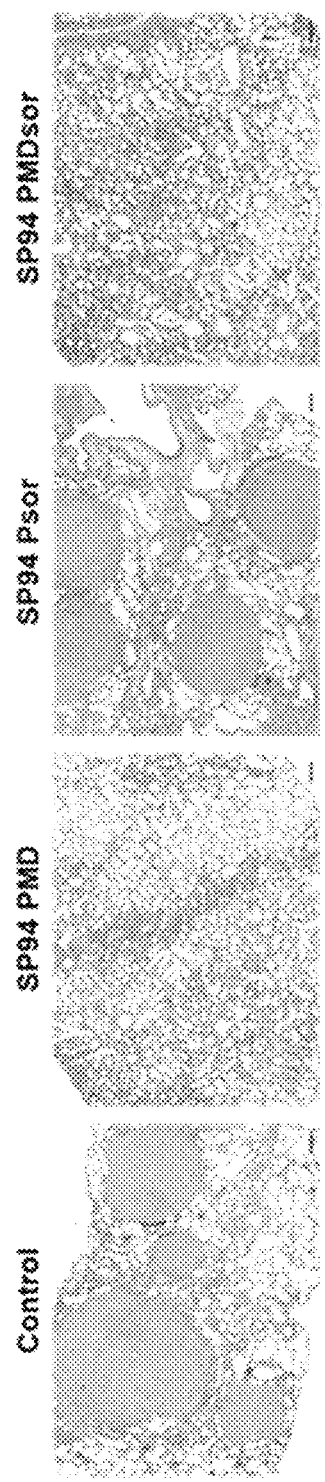
FIG. 8C is a dyed drawing showing the effect of the nanoparticles of the present invention on orthotopic tumor metastasis.

FIG. 8B is a schematic diagram showing the effect of the nanoparticles of the present invention on orthotopic tumor metastasis. FIG. 8C is a dyed drawing showing the effect of the nanoparticles of the present invention on orthotopic tumor metastasis. As shown in FIG. 8B and FIG. 8C, although SP94 Psor NPs moderately suppressed primary tumor growth, the occurrences of metastasis after the treatment of SP94 Psor NPs only slightly reduced compared with control group. However, amelioration of tumor hypoxia by delivery of the $MnO_2$ cores using both SP94 PMD and SP94 PMDsor NPs significantly decreased the amount of lung metastatic nodules.

Treatment of Sorafenib significantly induced an increase in intratumoral infiltration of tumor-associated macrophages (TAMs) which help tumor progression and metastasis. Moreover, the improvement of tumor oxygenation can not only enhance the immune activity by promoting T-cell proliferation and survival inside the tumor but also strengthen tumor vascular function via vessel normalization which facilitating T-cell tumor infiltration. Thus, the effect of various formulations of Sorafenib treatment on TAMs and $CD8^+$ T cells infiltration into tumors was evaluated by flow cytometry. Tumor-bearing mice were anesthetized first, perfused via intracardiac injection with PBS and then sacrificed. Tumor tissues were collected and harvested in enzyme-contained DMEM cell culture medium (1.5 mg/mL of collagenase type 1A and hyaluronidase). The tissues were cut and grinded into smaller pieces, and then digested for 1 hour at 37° C. to form the suspension of single tumor cell. The suspension was filtered through a 70-μm cell strainer (Corning, Manassas, Va.) and the cells were washed 3 times following by resuspending in cold flow buffer (1% BSA, 0.1% $NaN_3$ in PBS). Single-cell suspensions were incubated with the following monoclonal anti-mouse antibodies: F4/80-PE (eBiosciences, San Diego, Calif.), 7-AAD, CD3e-APC, CD8a-PE-Cy7, CD45-FITC and CD4-PE (BD Biosciences, East Rutherford, N.J.). Flow cytometry data were acquired on a BD FACSAria III flow cytometry and analyzed with FACSDiva™ software. The results are shown in FIG. 8D and FIG. 8E.

Figure 8D:
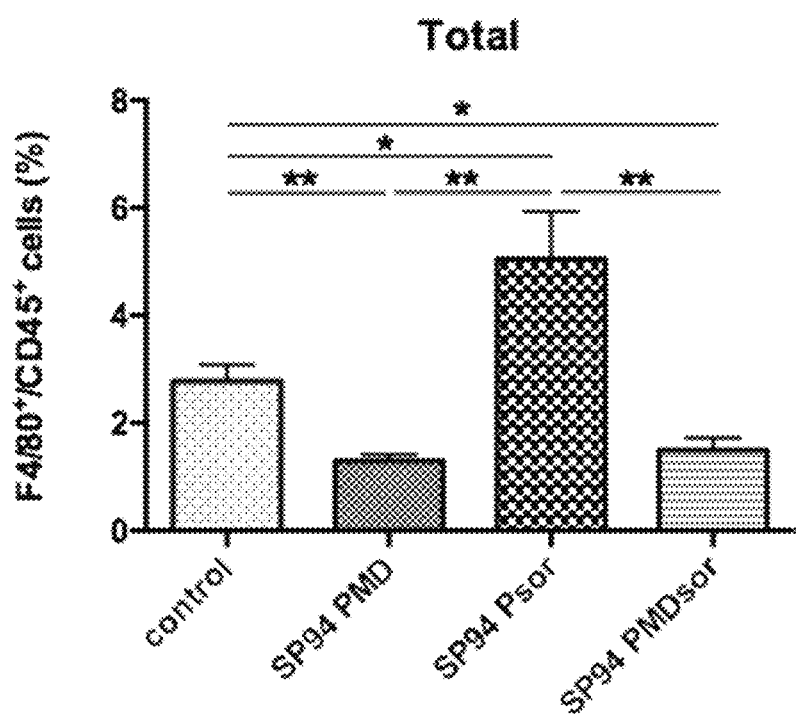
FIG. 8D is a schematic diagram showing the effect of the nanoparticles of the present invention on the infiltration of TAMs into tumors, wherein "*" indicates $p<0.05$; "**" indicates $p<0.01$.
Figure 8E:
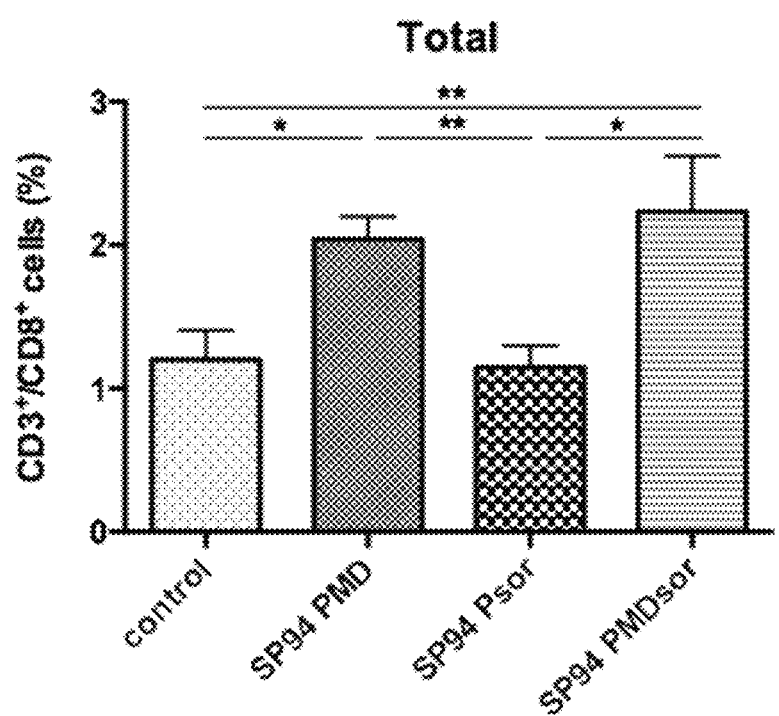
FIG. 8E is a schematic diagram showing the effect of the nanoparticles of the present invention on the infiltration of $CD8^+$ T cells into tumors, wherein "*" indicates $p<0.05$; "**" indicates $p<0.01$.

FIG. 8D is a schematic diagram showing the effect of the nanoparticles of the present invention on the infiltration of TAMs into tumors. FIG. 8E is a schematic diagram showing the effect of the nanoparticles of the present invention on the infiltration of $CD8^+$ T cells into tumors. As shown in FIG. 8D and FIG. 8E, in HCA-1 tumors, the infiltration of $F4/80^+$ TAMs significantly increased only in SP94 Psor-treated group, while the $CD8^+$ T cells remained at a basal level. In contrast, the significant decrease in TAMs and increase in $CD8^+$ T cells tumor infiltration were observed after treatment with SP94 PMD or SP94 PMDsor NPs, indicating that the TAMs infiltration might be suppressed and $CD8^+$ T cells infiltration might be facilitated by reducing tumor hypoxia.

As the result, the tumor vaccine was further combined with SP94 PMDsor NPs in the treatment. The fragment of codon-optimized GM-CSF (cGM-CSF) was amplified by PCR using the cGM-CSF forward primer: 5'-ACTC*GCTAGC*ATGGCCCACGAGAG-3' (SEQ ID No: 20) and reverse primer: 5'-CGT*GAATTC* TCACTTCTGCACGGG-3' (SEQ ID No: 21) incorporated NheI and EcoRI restrictions site in primer (underlined). p-cGM-CSF was constructed by digest restriction enzymes, ligated and cloned into the eukaryotic expression vector pcDNA3.1(−) (Invitrogen, Carlsbad, USA) plasmid. Strain DH5a was transformed with plasmids encoding cGM-CSF. Plasmids were next purified with PureLink™ HiPure Plasmid gigaprep kit (Thermo Fisher Scientific, USA). The plasmids were resuspended at 1 mg/ml in ddH2O and stored at −20° C. HCA-1 cells were seeded in 6 wells plate and attached overnight. The plasmids were mixed with Lipofectamine® 2000 (Thermo Fisher Scientific, USA) in the opti-mem medium. The mixture was added into the cells and incubated for 24 hours. The transfected cells were selected by G418 (300 μg/mL). After the selection, the cGM-CSF-overexpressing HCA-1cell line was obtained for vaccine production.

Whole liver cancer cell vaccine was generated from cGM-CSF-overexpressing HCA-1 cells. Cells were detached by EDTA and washed for three times. After washed, cells were resuspended in PBS ($10^7$ cells/mL) and incubated with mitomycin C (50 μg/mL) for 1 hour at 37° C. In the HCC tumor model, 3 days after tumor implantation, mice were injected i.p. five times (at 2- to 3-day intervals) with $5 \times 10^6$ mitomycin C-treated cells. On the 10th day after tumor implantation, tumor-bearing C3H/HeNCrNarl male mice were injected i.v. six times (three times per week) with SP94 PMDsor NPs (Sorafenib: 5 mg/kg, $MnO_2$:10 mg/kg). Two weeks after the first NPs treatment, mice were sacrificed and tumor volume was measured. The result is shown in FIG. 8F.

Figure 8F:
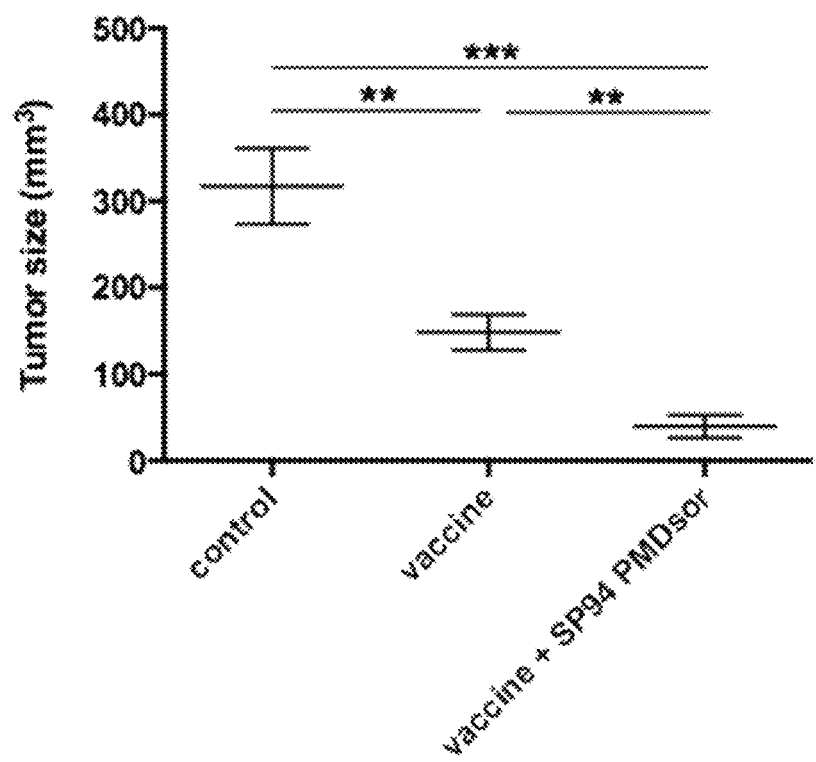
FIG. 8F is a schematic diagram showing whole cell vaccine therapy for combining the nanoparticles of the present invention with tumor vaccine, wherein "" indicates $p<0.01$; "*" indicates $p<0.001$.

FIG. 8F is a schematic diagram showing whole cell vaccine therapy for combining the nanoparticles of the present invention with tumor vaccine. As shown in FIG. 8F, although vaccine can moderately inhibited tumor growth, the combination with SP94 PMDsor NPs demonstrated better therapeutic efficacy. Therefore, the amelioration of tumor hypoxia by the NPs of the present invention can bring the benefits to tumor immunity and boost immunotherapy.

In summary, the nanoparticles of the present invention have the effect on good biocompatibility and stability, no damage to normal tissues, alleviation of tumor hypoxia, being used as an agonist for enhancing effect of a liver cancer drug, and as a contrast agent for cancer magnetic resonance imaging.

Although the present invention has been described with reference to the preferred embodiments, it will be apparent to those skilled in the art that a variety of modifications and changes in form and detail may be made without departing from the scope of the present invention defined by the appended claims.

---

What is claimed is:

1. A nanoparticle, comprising:
a core comprising manganese dioxide, at least one negatively charged lipid carrier, and an anti-angiogenesis drug, wherein the negatively charged lipid carrier encapsulates the manganese dioxide, and the core is encapsulated in a polymer and a lipid by a multiple phase emulsion reaction to form the nanoparticle, wherein the at least one negatively charged lipid carrier is 1,2-dioleoyl-sn-glycero-3-phosphate (DOPA), the anti-angiogenesis drug is hydrophobic, and the polymer is poly D,L-lactide-co-glycolic acid (PLGA).

2. The nanoparticle according to claim 1 has a particle diameter ranging from 20 nm to 500 nm.

3. The nanoparticle according to claim 1, wherein the anti-angiogenesis drug is Sorafenib.

4. The nanoparticle according to claim 1, wherein the lipid is an emulsifier or a stabilizer.

5. The nanoparticle according to claim 4, wherein the emulsifier is selected from the group consisting of D-α-Tocopherol polyethylene glycol 1000 succinate (TPGS), polyvinyl alcohol (PVA), and any combination thereof; and the stabilizer is selected from the group consisting of 1,2-distearoyl-sn-glycero-3-phosphoethanolamine-N-[methoxy (polyethylene glycol)-2000] (DSPE-PEG2000), 1,2-distearoyl-sn-glycero-3-phosphoethanolamine-N-[maleimide (polyethylene glycol)-2000] (DSPE-PEG Mal), cholesterol, 1,2-Dioleoyl-sn-glycero-3-phosphocholine (DOPC), and any combination thereof.

6. The nanoparticle according to claim 5, further comprising a target peptide, and the target peptide is a SP94 peptide.

7. The nanoparticle according to claim 1, wherein the core is a solid core.

8. The nanoparticle according to claim 1, which is applied in a contrast agent for magnetic resonance imaging.

9. A method for enhancing effect of a liver cancer drug, comprising administering to a subject in need thereof an agonist comprising an effective amount of the nanoparticle according to claim 1.

10. A method for ameliorating tumor hypoxia, comprising administering to a subject in need thereof a pharmaceutical composition comprising an effective amount of the nanoparticle according to claim 1.

11. The method according to claim 10, wherein the tumor hypoxia is liver tumor hypoxia.

12. The method according to claim 11, wherein the nanoparticle reverses epithelial-mesenchymal transition (EMT) induced by the liver tumor hypoxia.

* * * * *